US007960469B2

(12) United States Patent
Adachi et al.

(10) Patent No.: US 7,960,469 B2
(45) Date of Patent: *Jun. 14, 2011

(54) WATER ABSORBENT RESIN COMPOSITION AND PRODUCTION METHOD THEREOF

(75) Inventors: Yoshifumi Adachi, Himeji (JP); Takahiro Kitano, Himeji (JP); Shinichi Fujino, Himeji (JP); Katsuyuki Wada, Himeji (JP); Kazushi Torii, Himeji (JP); Taku Iwamura, Himeji (JP); Sayaka Machida, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/562,140

(22) PCT Filed: Jun. 23, 2004

(86) PCT No.: PCT/JP2004/009242
§ 371 (c)(1),
(2), (4) Date: Dec. 23, 2005

(87) PCT Pub. No.: WO2004/113452
PCT Pub. Date: Dec. 29, 2004

(65) Prior Publication Data
US 2007/0106013 A1    May 10, 2007

(30) Foreign Application Priority Data

Jun. 24, 2003  (JP) ................ 2003-180121
Sep. 19, 2003  (JP) ................ 2003-328635

(51) Int. Cl.
*C08L 33/00* (2006.01)
*C08F 220/04* (2006.01)
*C08K 3/10* (2006.01)
*C08K 3/08* (2006.01)
*C08L 29/04* (2006.01)

(52) U.S. Cl. ........ 524/556; 524/557; 524/379; 524/437; 524/441

(58) Field of Classification Search ............. 524/556, 524/557, 379, 437, 441, 2–10, 12–21, 23; 525/418
See application file for complete search history.

(56) References Cited

U.S. PATENT DOCUMENTS

| | | |
|---|---|---|
| 3,935,099 A | 1/1976 | Weaver et al. |
| 3,959,569 A | 5/1976 | Burkholder, Jr. |
| 4,043,952 A | 8/1977 | Ganslaw et al. |
| 4,076,663 A | 2/1978 | Masuda et al. |
| 4,093,776 A | 6/1978 | Aoki et al. |
| 4,124,748 A | 11/1978 | Fujimoto et al. |
| 4,286,082 A | 8/1981 | Tsubakimoto et al. |
| 4,367,323 A | 1/1983 | Kitamura et al. |
| 4,389,513 A | 6/1983 | Miyazaki |
| 4,446,261 A | 5/1984 | Yamasaki et al. |
| 4,558,091 A | 12/1985 | Hubbard |
| 4,587,308 A | 5/1986 | Makita et al. |
| 4,625,001 A | 11/1986 | Tsubakimoto et al. |
| 4,654,039 A | 3/1987 | Brandt et al. |
| 4,683,274 A | 7/1987 | Nakamura et al. |
| 4,771,105 A | 9/1988 | Shirai et al. |
| 4,873,299 A | 10/1989 | Nowakowsky et al. |
| 4,973,632 A | 11/1990 | Nagasuna et al. |
| 4,985,518 A | 1/1991 | Alexander et al. |
| 5,026,800 A | 6/1991 | Kimura et al. |
| 5,124,416 A | 6/1992 | Haruna et al. |
| 5,145,906 A | 9/1992 | Chambers et al. |
| 5,244,735 A | 9/1993 | Kimura et al. |
| 5,250,640 A | 10/1993 | Irie et al. |
| 5,264,495 A | 11/1993 | Irie et al. |
| 5,275,773 A | 1/1994 | Irie et al. |
| 5,380,808 A | 1/1995 | Sumiya et al. |
| 5,760,080 A | 6/1998 | Wada et al. |
| 5,837,789 A | 11/1998 | Stockhausen et al. |
| 5,843,575 A | 12/1998 | Wang et al. |
| 5,849,405 A | 12/1998 | Wang et al. |

(Continued)

FOREIGN PATENT DOCUMENTS

| | | |
|---|---|---|
| EP | 0456136 A2 | 11/1991 |
| EP | 0668080 A2 | 8/1995 |
| EP | 0811636 A1 | 12/1997 |
| EP | 0922717 A1 | 6/1999 |
| EP | 0 940 148 A1 | 9/1999 |
| EP | 0955086 A2 | 11/1999 |
| EP | 1 029 886 A2 | 8/2000 |
| EP | 1178059 A2 | 2/2002 |
| JP | 60-163956 | 8/1985 |
| JP | 61-46241 (A) | 3/1986 |
| JP | 62-7745 (A) | 1/1987 |
| JP | 63-270741 (A) | 11/1988 |
| JP | 64-56707 (A) | 3/1989 |

(Continued)

OTHER PUBLICATIONS

Decision to Grant A Patent for An Invention mailed Dec. 6, 2007 for counterpart Russian Application No. 2005140797/04(045428) with English translation.

*Primary Examiner* — Vasu Jagannathan
*Assistant Examiner* — Karuna P Reddy
(74) *Attorney, Agent, or Firm* — Harness, Dickey & Pierce, P.L.C.

(57) ABSTRACT

The production method of a water absorbent resin composition including a particulate water absorbent resin, wherein: 95 wt % or more of particles whose particle diameter is less than 850 μm and not less, than 106 μm are contained, and a weight average particle diameter of the particles is less than 500 μm and not less than 300 μm and a logarithmic standard deviation (σξ) of a particle size distribution is 0.45 or less, and a water-soluble component of the water absorbent composition is 35 wt % or less, and a multivalent metal component is contained, and an extraction rate of the multivalent metal component is 5.0 wt % or more and less than 100 wt %, thereby providing the water absorbent resin composition, free from any coagulation of particles in high humidity, which has superior absorbent property in terms of an absorbency and a diffusing absorbency under pressure.

24 Claims, 2 Drawing Sheets

U.S. PATENT DOCUMENTS

| | | | |
|---|---|---|---|
| 5,851,672 | A | 12/1998 | Wang et al. |
| 5,858,535 | A | 1/1999 | Wang et al. |
| 5,883,158 | A | 3/1999 | Nambu et al. |
| 6,054,541 | A | 4/2000 | Wada et al. |
| 6,071,976 | A | 6/2000 | Dairoku et al. |
| 6,087,002 | A | 7/2000 | Kimura et al. |
| 6,099,950 | A | 8/2000 | Wang et al. |
| 6,124,391 | A | 9/2000 | Sun et al. |
| 6,180,724 | B1 | 1/2001 | Wada et al. |
| 6,228,930 | B1 | 5/2001 | Dairoku et al. |
| 6,232,520 | B1 | 5/2001 | Hird et al. |
| 6,254,990 | B1 | 7/2001 | Ishizaki et al. |
| 6,300,275 | B1 | 10/2001 | Weir |
| 6,323,252 | B1 | 11/2001 | Gartner et al. |
| 6,562,743 | B1 | 5/2003 | Cook et al. |
| 6,562,879 | B1 * | 5/2003 | Hatsuda et al. ............... 521/56 |
| 6,586,549 | B1 | 7/2003 | Hatsuda et al. |
| 6,605,673 | B1 * | 8/2003 | Mertens et al. .......... 525/329.5 |
| 6,620,889 | B1 | 9/2003 | Mertens et al. |
| RE38,444 | E | 2/2004 | Wada et al. |
| 6,831,142 | B2 | 12/2004 | Mertens et al. |
| 6,951,895 | B1 | 10/2005 | Qin et al. |
| 2002/0120074 | A1 | 8/2002 | Wada et al. |
| 2002/0128618 | A1 | 9/2002 | Frenz et al. |
| 2004/0071966 | A1 | 4/2004 | Inger et al. |
| 2004/0106745 | A1 * | 6/2004 | Nakashima et al. ......... 525/418 |

FOREIGN PATENT DOCUMENTS

| | | |
|---|---|---|
| JP | 3-179008 (A) | 8/1991 |
| JP | 4-46617 (B2) | 7/1992 |
| JP | 5-40780 | 6/1993 |
| JP | 6-57010 (A) | 3/1994 |
| JP | 6-107846 (A) | 4/1994 |
| JP | 08-057311 | 3/1996 |
| JP | 8-176311 (A) | 7/1996 |
| JP | 9-124879 (A) | 5/1997 |
| JP | 9-509591 | 9/1997 |
| JP | 9-309916 A | 12/1997 |
| JP | 10-147724 (A) | 6/1998 |
| JP | 11-240959 A | 9/1999 |
| JP | 11-240959 (A) | 9/1999 |
| JP | 11-315147 A | 11/1999 |
| JP | 11-315147 (A) | 11/1999 |
| JP | 2000-302876 A | 10/2000 |
| JP | 2000-302876 (A) | 10/2000 |
| JP | 2001-096151 A | 4/2001 |
| JP | 2001-96151 (A) | 4/2001 |
| JP | 2001-098170 A | 4/2001 |
| JP | 2001-98170 (A) | 4/2001 |
| JP | 2001-252307 (A) | 9/2001 |
| JP | 2001-523287 (A) | 11/2001 |
| JP | 2001-523289 (A) | 11/2001 |
| JP | 2002-523526 (A) | 7/2002 |
| JP | 2002-538275 (A) | 11/2002 |
| JP | 2002-539281 (A) | 11/2002 |
| JP | 2003-105092 A | 4/2003 |
| JP | 2003-105092 (A) | 4/2003 |
| JP | 2003-165883 A | 6/2003 |
| JP | 2003-165883 (A) | 6/2003 |
| JP | 2003-523484 (A) | 8/2003 |
| JP | 2003-529647 (A) | 10/2003 |
| RU | 2 183 648 C2 | 6/2002 |
| RU | 2 193 045 C2 | 11/2002 |
| WO | WO 95/22355 | 8/1995 |
| WO | WO 95/22356 | 8/1995 |
| WO | WO 95/22358 | 8/1995 |
| WO | WO 98/37149 | 8/1998 |
| WO | WO 98/48857 | 11/1998 |
| WO | WO 98/49221 | 11/1998 |
| WO | WO 99/55767 A | 11/1999 |
| WO | WO 00/10619 | 3/2000 |
| WO | WO 00/38607 A1 | 7/2000 |
| WO | WO 00/53644 | 9/2000 |
| WO | WO 00/53664 | 9/2000 |
| WO | WO 01/74913 A1 | 10/2001 |
| WO | WO 02/20068 A1 | 3/2002 |
| WO | WO 02/22717 A1 | 3/2002 |
| WO | WO 02/100451 A2 | 12/2002 |
| WO | WO 02/100451 A3 | 12/2002 |
| WO | WO 2004/069293 A1 | 8/2004 |
| WO | WO 2004/069915 A2 | 8/2004 |

* cited by examiner

WATER ABSORBENT RESIN COMPOSITION AND PRODUCTION METHOD THEREOF

TECHNICAL FIELD

The present invention relates to a water absorbent resin and a production method thereof. More specifically, the present invention relates to (i) a water absorbent resin composition favorably used in disposable paper diapers, pads, or women's sanitary napkins, and (ii) a production method of the water absorbent resin composition.

BACKGROUND ART

Recently, a water absorbent resin is widely used as a main component of sanitary materials (absorbent articles) such as paper diapers, sanitary napkins, incontinence pads and the like, in order to absorb body fluids (e.g. urine and blood).

Well-known examples of the water absorbent resin are (i) cross-linked partially neutralized polyacrylic acid; (ii) a hydrolyzed starch-acrylonitrile graft polymer; (iii) a neutralized starch-acrylic graft polymer; (iv) a saponified vinyl acetate-acrylic ester copolymer; (v) cross-linked carboxymethylcellulose; (vi) hydrolyzed acrylonitrile copolymer or hydrolyzed acrylamide copolymer, or cross-linked acrylonitrile copolymer or cross-linked acrylamide copolymer; (vii) a cross-linked cationic monomer, (viii) a cross-linked isobutylene-maleic acid copolymer; (ix) a cross-linked body of 2-acrylamide-2-methylpropanesulfonic acid and acrylic acid; (x) and the like.

The water absorbent resin has a high absorbency with respect to an aqueous liquid. However, due to its high absorbency, the water absorbent resin absorbs also moisture in air (moisture absorption). Thus, particles of the water absorbent resin are coagulated with each other, which results in a blocking phenomenon in which the water absorbent resin loses fluidity as powder. The moisture absorption blocking phenomenon raises the following problems: at the time of production of the water absorbent resin and at the time of production of a sanitary material such as a disposable paper diaper using the water absorbent resin, the blocking phenomenon occurs in a storage hopper or a transportation line, or the water absorbent resin adheres to a production apparatus, so that the blocking or adhering water absorbent resin becomes much less treatable. As a result, it is impossible to stably manufacture the product. Then, in order to prevent the blocking phenomenon occurring at the time of moisture absorption, a method in which an inorganic compound is added to the water absorbent resin is conventionally adopted.

Examples of the method are: a method in which an inorganic powder is mixed with such a water absorbent resin that approximately 60 wt % or less polymer particles pass through a sieve of 300 µm in mesh (Published Japanese Translations of International Publication of Patent Application No. 523526/2002 (Tokuhyo 2002-523526)); a water-insoluble water absorbent resin composition obtained by adding water to a mixture of multivalent metal salt and a water absorbent resin (Japanese Examined Patent Publication of Patent Application No. 4667/1992 (Tokukohei 4-4667)); a production method in which water containing a multivalent metal salt is sprayed to a water absorbent resin (Japanese Examined Patent Publication of Patent Application No. 40780/1993 (Tokukohei 5-40780)); a water absorbent resin modified by adding water containing a multivalent metal salt to a surface of a water absorbent resin whose particle size ranges from 5 to 500 µm and by heating the water absorbent resin (Japanese Unexamined Patent Publication No. 46241/1986 (Tokukaisho 61-46241)); a water absorbent resin modified by adding water, in which inorganic salt has been dissolved, to a water absorbent resin whose surface has been cross-linked (Japanese Unexamined Patent Publication No. 124879/1997 (Tokukaihei 9-124879)); a water absorbent agent, obtained by adding a multivalent metal compound to a water absorbent resin, in which multivalent metal locally exists in a vicinity of a surface of the water absorbent agency (Japanese Unexamined Patent Publication No. 96151/2001 (Tokukai 2001-96151)); and the like.

Further, examples of a method in which an inorganic compound is added to the water absorbent resin in order to improve a water-absorbing ability of the water absorbent resin powder include: a method in which a multivalent metal salt such as aluminum sulfate and a water absorbent resin are dry-blended and thus obtained mixture is brought into contact with a binding agent (water or the like) so as to produce such a water absorbent resin that a gel having absorbed water has elasticity and a gel blocking phenomenon hardly occurs (Published Japanese Translations of International Publication of Patent Application No. 523289/2001 (Tokuhyo 2001-523289)); a composition obtained by adding an aqueous solution containing multivalent metal salt to a water absorbent resin that has been thermally processed at more than 170° C. for more than 10 minutes (Published Japanese Translations of International Publication of Patent Application No. 523287/2001 (Tokuhyo 2001-523287)); a water-insoluble swelling hydrogel obtained by coating a water-insoluble swelling hydrogel, having specific absorbency under pressure and having gel strength, with a three-dimensional or electrostatic spacer (U.S. Patent No. 2002/0128618); a water absorbent resin secondarily cross-linked by an organic surface cross-linking agent aqueous solution and a cation aqueous solution (Published Japanese Translations of International Publication of Patent Application No. 538275/2002 (Tokuhyo 2002-538275)); and the like.

However, according to these known methods, it is impossible to sufficiently improve a moisture absorption blocking property, and an absorbency and a diffusing absorbency under pressure may significantly drop. Further, it is impossible to sufficiently improve an anti-moisture-absorption-blocking property while suppressing drop in the absorbent properties (for example, an absorbency, a diffusing absorbency under pressure, and the like) of the water absorbent resin.

Recently, the sanitary material such as the sanitary napkin and the like using the water absorbent resin has higher performance and a thinner size, and an amount of the water absorbent resin used for each sanitary material tends to increase, and also a weight % of the water absorbent resin tends to increase with respect to the whole absorber constituted of the water absorbent resin and a hydrophilic fiber. That is, by using (i) a smaller amount of a hydrophilic fiber whose bulk density is low and (ii) a larger amount of a water absorbent resin having a superior water absorbent property and high bulk density, a ratio of the water absorbent resin contained in the absorber is increased, thereby making the sanitary material thinner without decreasing an amount of water absorption.

The sanitary material which includes a smaller amount of the hydrophilic fiber and a larger amount of the water absorbent resin is preferable merely in terms of liquid storage, but raises problems in terms of distribution and diffusion of liquid in actual use in diapers.

That is, when a large amount of the water absorbent resin is used, the water absorbent resin becomes soft and gelatinous upon absorbing water. This causes a gel blocking phenomenon. As a result, a liquid diffusing property of the diaper significantly drops. In order to avoid such phenomenon and to keep the absorbent property of the absorber high, a ratio of the hydrophilic fiber and the water absorbent resin is limited, so that there is a limit in making the sanitary material thinner.

As means for improving the liquid diffusing property of the diaper while preventing the gel blocking in the diaper, there are proposed: a method in which two types of water absorbent resins different from each other in terms of the water absorbent property are used (Japanese Unexamined Patent Publication No. 252307/2001 (Tokukai 2001-252307)); a method in which a composition containing a cationic ion exchange hydrogel formation polymer and an anionic ion exchange hydrogel formation polymer is used (WO 98/37149 pamphlet); a method in which a water absorbent resin having high cross-linking density in its surface is used (Japanese Unexamined Patent Publication No. 057010/1994 (Tokukaihei 6-057010)); and the like. However, in these methods, there is a room for improving the absorbent property as an absorber having a high water absorbent resin density.

Further, it is well known that a water absorbent resin is treated with a metal compound so as to improve a liquid diffusing property of water absorbent resin powder. Examples of the method include: a method in which multivalent metal salt such as aluminum sulfate is dry-blended with a water absorbent resin, and is brought into contact with a binding agent (water or the like), thereby producing a water absorbent resin, having elasticity, which hardly causes the gel blocking (WO 98/48857 pamphlet); a method in which a water absorbent resin is secondarily cross-linked with a water-soluble organic surface cross-linking agent and water-soluble cation (Tokuhyo 2002-538275 and Tokuhyo 2002-539281); a high water absorbent resin composition which includes a high water absorbent resin and fine powder made up of hydrated oxides at least partially containing two types of metals (M1 and M2) so as to have a -M1-O-M2- bond (Japanese Unexamined Patent Publication No. 147724/1998 (Tokukaihei 10-147724)); and the like.

In accordance with the various known methods, efforts have been made so as to improve (i) the gel blocking property or (ii) liquid permeability/liquid diffusing property. However, a water absorbent resin which improves these two properties (the gel blocking property and the liquid permeability/liquid diffusing property) at the same time has not been invented.

Further, in order to produce a water absorbent resin composition which is superior in the gel blocking property and the liquid permeability/liquid diffusing property, it is necessary that surfaces of particles of the water absorbent resin are secondarily cross-linked evenly. When the surfaces of the particles are not secondarily cross-linked evenly, portions which are not secondarily cross-linked to each other are clumped, so that the blocking phenomenon occurs. As a result, a production apparatus is blocked up, so that it is impossible to stably produce the water absorbent resin.

DISCLOSURE OF INVENTION

The present invention was devised in view of the foregoing conventional problems, and the object of the present invention is to provide (i) a water absorbent resin composition which is free from any clump of particles even in high humidity and is superior in absorbent properties such as an absorbency and a diffusing absorbency under pressure and has particles whose surfaces are secondarily cross-linked evenly, and (ii) a production method of the water absorbent resin composition.

In terms of a superior absorbent property and a superior moisture absorption blocking property which suppresses clump of particles in high humidity, the inventors of the present invention earnestly studied a water absorbent resin. As a result of the earnest study, they found that: it is possible to achieve the foregoing object by giving the water absorbent resin (1) a specific cross-linking structure, (2) a specific particle size distribution, and (3) a metal component, and by arranging the water absorbent resin so that an extraction rate of a multivalent metal component is 5 wt % (wt %) or more and less than 100 wt %, thereby devising the present invention.

That is, the water absorbent resin composition of the present invention is a water absorbent resin composition, whose main component is a particulate water absorbent resin (A) having a cross-linking structure obtained by polymerizing an unsaturated monomer containing an acid group, said particulate water absorbent resin (A) being cross-linked in a vicinity of a surface of the water absorbent resin (A), wherein: the water absorbent resin composition contains 95 wt % or more of particles whose particle diameter is less than 850 μm and not less than 106 μm, and a weight average particle diameter of the particles is less than 500 μm and not less than 300 μm, and a logarithmic standard deviation ($\sigma\zeta$) of a particle size distribution of the water absorbent resin composition is 0.45 or less, and a water-soluble component of the water absorbent composition is 35 wt % or less, and the water absorbent resin composition includes a multivalent metal component, and an extraction rate of the multivalent metal component is 5.0 wt % or more and less than 100 wt %.

Further, in the water absorbent resin composition of the present invention, it is preferable that the particulate water absorbent resin (A) is a particulate water absorbent resin in which the vicinity of the surface is further cross-linked by a surface cross-linking agent containing a polyol.

Further, in the water absorbent resin composition of the present invention, it is preferable that a moisture absorption blocking ratio a is 30% or less when the water absorbent resin composition is left at 25° C. in a relative humidity of 90% for an hour.

Further, in the water absorbent resin composition of the present invention, it is preferable that: a centrifuge retention capacity (CRC) at which the water absorbent resin composition absorbs 0.90 wt % of a physiological saline without load for 30 minutes is 25 g/g or more, and a diffusion absorbency under pressure (DAP) at which the water absorbent resin composition absorbs 0.90 wt % of a physiological saline at 1.9 kPa for 60 minutes is 20 g/g or more.

Further, the absorber of the present includes the water absorbent resin composition and a hydrophilic fiber so that an amount of the water absorbent resin composition (core concentration) is 20 wt % or more with respect to a total amount of the water absorbent resin composition and the hydrophilic fiber.

Further, the absorbent article of the present invention includes the absorber, a liquid-permeable surface sheet, and a liquid-impermeable back sheet.

Further, the method of the present invention for producing the water absorbent resin composition includes the steps of: adding a solution of an aqueous multivalent metal compound (B) to a particulate water absorbent resin (A), having a cross-linking structure obtained by polymerizing an unsaturated monomer containing an acid group, which is cross-linked in a vicinity of a surface of the particulate water absorbent resin (A); and mixing the solution of the aqueous multivalent metal compound (B) with the particulate water absorbent resin (A), wherein: the particulate water absorbent resin (A) contains 95 wt % or more of the particles whose particle diameter is less than 850 μm and not less than 106 μm, and a weight average particle diameter of the particles is less than 500 μm and not less than 300 μm, and a logarithmic standard deviation (σζ) of a particle size distribution of the particulate water absorbent resin (A) is 0.45 or less, and a water-soluble component of the particulate water absorbent resin (A) is 35 wt % or less, and an amount of a multivalent metal component contained in the solution of the aqueous multivalent metal compound (B) is 0.001 to 10 wt. % with respect to the particulate water absorbent resin (A), and a concentration of the aqueous multivalent metal compound (B) in the solution is 0.40 or more with respect to a saturated concentration of the aqueous multivalent metal compound (B) in the solution, and temperature of the particulate water absorbent resin (A) is 50° C. or higher and lower than 100° C., and/or temperature of the solution of the aqueous multivalent metal compound (B) is 30° C. or higher and lower than 100° C.

The inventors of the present invention earnestly studied the water absorbent resin composition so as to realize (i) a superior moisture absorption blocking property which less causes particles to clump in high humidity and (ii) a superior liquid permeation/liquid diffusing property at the same time. As a result, they found it possible to achieve the foregoing object by arranging the method so as to includes the steps of: mixing a particulate water absorbent resin whose main component is a polymer having a cross-linking structure obtained by polymerizing acrylic acid and/or its salt, a specific amount of an aqueous solution of a multivalent metal compound, and an organic surface cross-linking agent; and heating a mixture obtained in the mixing step at 150 to 300° C., so as to cross-link a vicinity of a surface of the particulate water absorbent resin, wherein the particulate water absorbent resin has a specific particle size distribution, and a concentration of a multivalent metal component contained in the aqueous solution of the multivalent metal compound (B) is 1.80 wt % or more. Unexpectedly, the inventors of the present invention found that: the water absorbent resin composition treated by using a surface treatment agent whose concentration of a multivalent metal component is high has a much higher saline flow conductivity (SFC: indicative of a liquid permeation rate under pressure) than that of a water absorbent resin composition whose surface is treated with a surface treatment agent having a known concentration.

Further, in order to realize a superior moisture absorption blocking property and a superior liquid permeation/liquid diffusing property in the water absorbent resin at the same time, it is necessary that particle surfaces are secondarily cross-linked evenly. The inventors of the present invention found that: in order to achieve the object, it is necessary that a precursor has a superior fluidity (humidification blocking property). Note that, the precursor of the present invention is a mixture of the particulate water absorbent resin, the aqueous solution of the multivalent metal compound, and the organic surface cross-linking agent. Further, the humidification of the present invention means to mix an aqueous solution of a multivalent metal compound and an organic surface cross-linking agent with a particulate water absorbent resin. Further, the saline of the present invention is an aqueous solution obtained by dissolving sodium chloride in water.

That is, the method of the present invention for producing the water absorbent resin composition includes the steps of: mixing a particulate water absorbent resin (A) having a cross-linking structure obtained by polymerizing an unsaturated monomer containing an acid group, a solution of an aqueous multivalent metal compound (B), and an organic surface cross-linking agent (C); and heating a mixture that has been obtained in the mixing step at 150 to 300° C. so as to cross-link a vicinity of a surface of the particulate water absorbent resin (A), wherein: the particulate water absorbent resin (A) contains 95 wt % or more of the particles whose particle diameter is less than 850 μm and not less than 106 μm, and a logarithmic standard deviation (σζ) of a particle size distribution of the particulate water absorbent resin (A) is 0.45 or less, and an amount of a multivalent metal component contained in the solution of the aqueous multivalent metal compound (B) is 0.001 to 10 wt % with respect to the particulate water absorbent resin (A), and a concentration of the multivalent metal component contained in the solution of the aqueous multivalent metal compound (B) is at least 1.80 wt %.

Further, the method of the present invention for producing the water absorbent resin composition includes the step of heating a precursor (D) obtained by mixing a particulate water absorbent resin (A) having a cross-linking structure obtained by polymerizing an unsaturated monomer containing an acid radical, a solution of a multivalent metal compound (B), and an organic surface cross-linking agent at 150 to 300° C. so as to cross-link a vicinity of a surface of the particulate water absorbent resin (A), wherein: the particulate water absorbent resin (A) contains 95 wt % or more of the particles whose particle diameter is less than 850 μm and not less than 106 μm, and a logarithmic standard deviation (σζ) of a particle size distribution of the particulate water absorbent resin (A) is 0.45 or less, and an amount of a multivalent metal component contained in the solution of the multivalent metal compound (B) is 0.001 to 10 wt % with respect to the particulate water absorbent resin (A), and a humidification blocking ratio (wt %) of the precursor (D) is 80 wt % or less.

Further, in the method of the present invention for producing the water absorbent resin composition, it is preferable that a main component of the water absorbent resin composition is a polymer having a cross-linking structure obtained by polymerizing acrylic acid and/or salt thereof.

Further, in the method of the present invention for producing the water absorbent resin composition, it is preferable that a concentration of the multivalent metal component contained in the solution of the multivalent metal compound (B) is at least 1.80 wt %.

Further, in the method of the present invention for producing the water absorbent resin composition, it is preferable that the solution of the multivalent metal compound (B) and/or the organic surface cross-linking agent is heated at 30° C. or higher.

Further, in the method of the present invention for producing the water absorbent resin composition, it is preferable that the organic surface cross-linking agent includes a multivalent alcohol.

Further, in the method of the present invention for producing the water absorbent resin composition, it is preferable that the multivalent metal component of the multivalent metal compound (B) includes one or more metals selected from bivalent or further multivalent typical metals and transition metals whose group numbers are 4 to 12.

Further, in the method of the present invention for producing the water absorbent resin composition, it is preferable that the multivalent metal component of the multivalent metal compound (B) is aluminum.

For a fuller understanding of the nature and advantages of the invention, reference should be made to the ensuing detailed description taken in conjunction with the accompanying drawings.

BEST MODE FOR CARRYING OUT THE INVENTION

Embodiment 1

Figure 1:
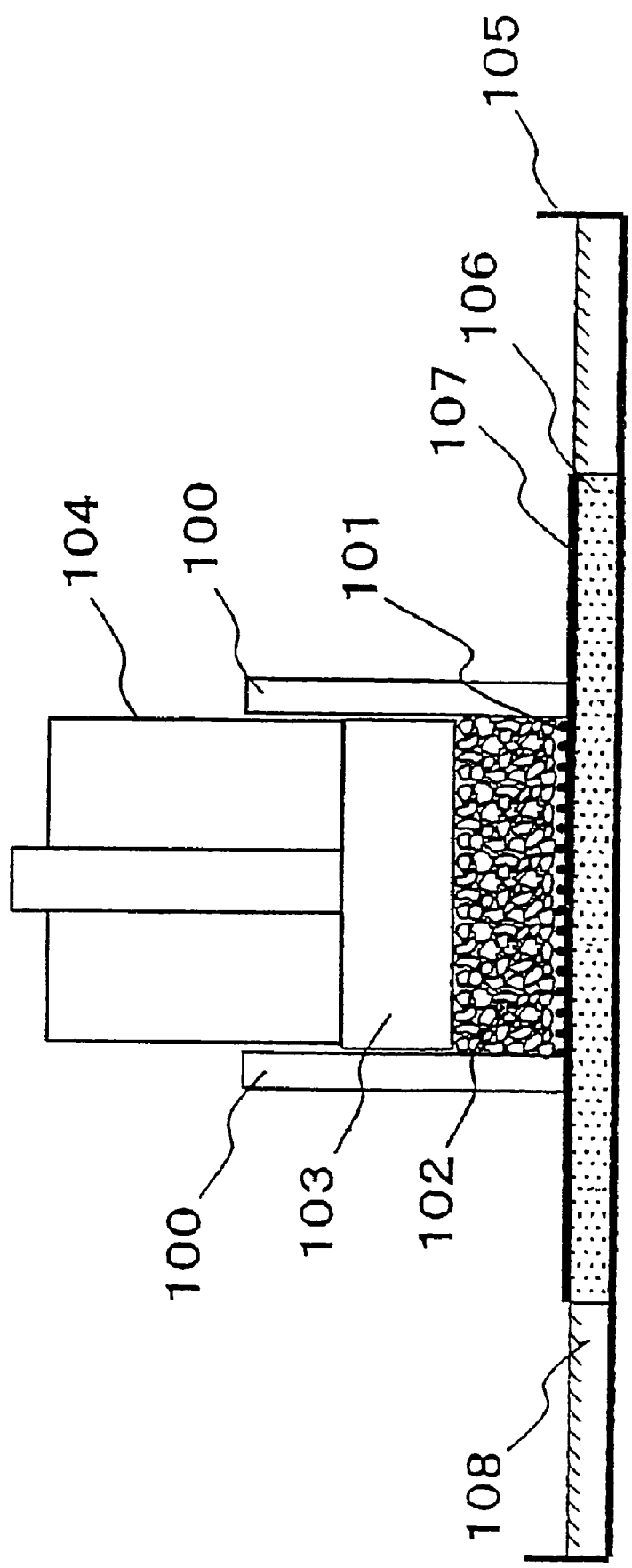
FIG. 1 is a cross sectional view schematically showing a measuring apparatus used to measure an absorbency against pressure (AAP) of the water absorbent resin composition.

A water absorbent resin composition according to the present embodiment includes a particulate water absorbent resin (A) and a multivalent metal component (B). Note that, the water absorbent resin composition of the present embodiment is a composition which includes a water absorbent resin as a main component, and includes 80 to 100 wt % of the water absorbent resin, more preferably 90 to 100 wt % of the water absorbent resin. The water absorbent resin composition is favorably used in sanitary materials such as paper diapers, sanitary napkins, incontinence pads, medical pads, and the like. The following description will detail (I) the water absorbent resin (A) and (II) the multivalent metal component (B).

(I) Particulate Water Absorbent Resin (A)

The "particulate water absorbent resin (A)" is constituted of spherical or amorphous particles of water-insoluble water-swelling hydrogel formation polymer (hereinafter, referred to also as a water absorbent resin) which can be obtained by polymerizing a hydrophilic monomer. The water-swelling property means a condition under which the water absorbent resin necessarily absorbs a large amount of water whose weight is five times as much as a weight of the water absorbent resin itself, preferably 50 to 1000 times as much as the weight of the water absorbent resin itself, in an ion exchange water. The water-insoluble property means a condition under which 5 wt % or more and 50 wt % or less, more preferably 5 wt % or more and 25 wt % or less, further more preferably 5 wt % or more and 20 wt % or less, particularly preferably 5 wt % or more and 15 wt % or less, most preferably 5 wt % or more and 10 wt % or less of a water-soluble component (water-soluble polymer) is contained in the water absorbent resin. Further, the water-insoluble water-swelling hydrogel formation polymer has a spherical or indeterminate particulate shape.

Specific examples of the water-insoluble water-swelling hydrogel formation polymer includes: a partially neutralized cross-linked polyacrylic acid polymer (U.S. Pat. No. 4,625,001, U.S. Pat. No. 4,654,039, U.S. Pat. No. 5,250,640, U.S. Pat. No. 5,275,773, European Patent No. 456136, and the like); a cross-linked partially neutralized starch-acrylic acid graft polymer (U.S. Pat. No. 4,076,663); an isobutylene-maleic acid copolymer (U.S. Pat. No. 4,389,513); a saponified vinyl acetate-acrylic acid copolymer (U.S. Pat. No. 4,124,748); a hydrolyzed acrylamide (co)polymer (U.S. Pat. No. 3,959,569); a hydrolyzed acrylonitril copolymer (U.S. Pat. No. 3,935,099); and the like. However, the water absorbent resin of the present embodiment is constituted of a cross-linked polyacrylic acid (salt) polymer including acrylic acid and/or salt thereof as a main component. Note that, the "main component" of the present embodiment is defined as follows: in case where a certain component "a" is included in "B", as long as "B" includes 30 wt % or more of the component "a" with respect to the whole amount of "B", the component "a" is a main component of "B". The cross-linked polyacrylic acid (salt) polymer of the present embodiment is a cross-linked polymer in which 50 mol % or more and 100 mol % or less of acrylic acid and/or salt thereof is included in a monomer component, preferably 70 mol % or more and 100 mol % or less, more preferably 90 mol % or more and 100 mol % or less of acrylic acid and/or salt thereof is included in the monomer component. Further, it is preferable that 50 to 90 mol %, preferably 60 to 80 mol % of an acid radical contained in the polymer is neutralized, and examples of the salt include: alkali metal salt such as sodium, potassium, and lithium; ammonium salt; and amine salt, and it is preferable to use sodium salt. The water absorbent resin for forming salt may be neutralized in a monomer phase before polymerization, or may be neutralized during and after polymerization, or these processes may be combined with each other.

Further, in the present embodiment, as the particulate water absorbent resin (A), it is possible to use a water absorbent resin having a cross-linking structure obtained by polymerizing an unsaturated monomer containing an acid radical, in terms of the absorbent property. Note that, the unsaturated monomer containing an acid group used in the present embodiment includes a monomer containing an acid group in polymerization and a monomer such as acrylonitrile which becomes an acid group by being hydrolyzed after polymerization.

Examples of the water absorbent resin are one kind or two or more kinds of: partially neutralized polyacrylic acid polymer; hydrolyzed starch-acrylonitrile graft polymer; starch-acrylic acid graft polymer; saponified vinyl acetate-acrylic acid ester copolymer; hydrolyzed acrylonitrile copolymer or hydrolyzed acrylamide copolymer, or cross-linked acrylonitrile copolymer or cross-linked acrylamide copolymer; denaturated carboxyl-group-containing cross-linked polyvinyl alcohol; cross-linked isobutylene-maleic anhydride copolymer; and the like. It is preferable to use partially neutralized polyacrylic acid polymer obtained by polymerizing and cross-linking a monomer containing acrylic acid and/or its salt (neutralized acrylic acid) as a main component.

The partially neutralized polyacrylic acid polymer may be obtained by copolymerizing a monomer (acrylic acid and/or salt thereof) used as a main component with other monomer as required. Specific examples of other monomer include: an anionic unsaturated monomer such as methacrylic acid, fumaric acid, crotonic acid, itaconic acid, maleic acid, vinyl sulfonic acid, styrene sulfonic acid, 2-(meth)acrylamide-2-methylpropane sulfonic acid, 2-(meth)acryloylethane sulfonic acid, 2-(meth)acryloylepropane sulfonic acid, and salt thereof; a nonionic hydrophilic-group-containing unsaturated monomer such as N-vinyl-2-pyridone, N-vinyl acetamide, methoxypolyethylene glycol(meth)acrylate, polyethylene glycol (meth) acrylate, isobutylene, lauryl(meth)acrylate, acrylamide, (meth)acrylamide, N-ethyl(meth)acrylamide, N-n-propyl (meth)acrylamide, N-isopropyl(meth)acrylamide, N,N-dimethyl (meth) acrylamide, 2-hydroxyethyl(meth) acrylate, 2-hydroxypropyl(meth)acrylate, methoxypolyethyleneglycol (meth)acrylate, polyethyleneglycol mono(meth)acrylate, vinylpyridine, N-vinylpyrrolidone, N-acryloylpiperidine, and N-acryloylpyrrolidine; and cationic unsaturated monomer such as N,N-dimethylaminoethyl(meth)acrylate, N,N-diethylaminoethyl(meth)acrylate, N,N-dimethylaminopropyl(meth)acrylate, N,N-dimethylaminopropyl(meth)acrylamide, and quaternary salt thereof; and the like.

Ordinarily, an amount of the monomer other than acrylic acid is 0 to 30 mol %, preferably 0 to 10 mol %, with respect to all the monomers (contained in the water absorbent resin), thereby further improving an absorbent property of a product water absorbent resin (composition) and producing the water absorbent resin (composition) at lower cost.

Examples of a method for introducing a cross-linking structure into the water absorbent resin used in the present embodiment are as follows: self cross-linking is proceeded without using a cross-linking agent; not only the monomer but also an internal cross-linking agent having two or more polymerizable unsaturated groups or two or more reactive groups is copolymerized or reacted with the particulate water absorbent resin; and a similar manner. It is preferable to copolymerize or react the internal cross-linking agent.

Examples of the internal cross-linking agent include: N,N'-methylenebis(meth)acrylamide, (poly)ethyleneglycol di(meth)acrylate, (poly)propyleneglycol di(meth)acrylate, trimethylolpropanetri(meth)acrylate, glycerinetri(meth)acrylate, glycerineacrylatemethacrylate, ethyleneoxide denatured trimethylolpropanetri(meth)acrylate, pentaerythritolhexa(meth)acrylate, triallyl cyanurate, triallyl isocyanurate, triallyl phosphate, triallyl amine, poly(meth)allyloxyalkane, (poly)ethyleneglycol diglycidyl ether, glycerol diglycidyl ether, glycerol triglycidyl ether, ethylene glycol, polyethylene glycol, propylene glycol, glycerine, pentaerythritol, ethylenediamine, ethylene carbonate, propylene carbonate, polyethyleneimine, glycidyl(meth)acrylate, and the like.

These internal cross-linking agents may be used either independently or in a suitable combination of two or more kinds. The internal cross-linking agent may be added to the reaction system either at once or in separate doses. When using one or more internal cross-linking agents, it is preferable that a cross-linking monomer including not less than two polymerizable unsaturated groups is always used for the polymerization, taking into account the absorption characteristics or other properties of the product water absorbent or the product water absorbent resin composition.

An amount of internal cross-linking agent used is preferably 0.001 to 3 mol %, more preferably 0.001 to 2 mol %, further more preferably 0.005 to 2 mol %, still more preferably 0.005 to 0.5 mol %, further still more preferably 0.01 to 1 mol %, particularly preferably 0.01 to 0.2 mol %, more particularly preferably 0.03 to 0.15 mol %, and most preferably 0.03 to 0.5 mol %, with respect to a total number of moles of all the unsaturated monomers (excluding the cross-linking agent). In case where the amount of the internal cross-linking agent used is less than 0.001 mol %, or in case where the internal cross-linking agent exceeds 3 mol %, it may be impossible to obtain the sufficient absorbent property.

When the internal cross-linking agent is used to form a cross-linking structure inside the water absorbent resin, the internal cross-linking agent is added to the reaction system before, during, or after the polymerization of the unsaturated monomer, or after the neutralization of the unsaturated monomer or the polymer. Note that, in the polymerization, it is possible to add (i) for example 0 to 30 wt % (with respect to the monomer) of hydrophilic polymers such as a mixture of starch and cellulose, a derivative of starch and cellulose, polyvinyl alcohol, polyacrylic acid (salt), cross-linked polyacrylic acid (salt), and the like or (ii) for example 0 to 5 wt % (with respect to the monomer) of a chain transfer agent such as hypophosphorous acid (salt).

In polymerizing the aforementioned monomer so as to obtain the water absorbent resin used in the present embodiment, bulk polymerization or precipitation polymerization may be performed. However, in terms of (i) performance of the water absorbent resin, (ii) controllability of polymerization, and (iii) absorbent properties of a swelling gel, more preferable methods of polymerization are aqueous polymerization and reversed suspension polymerization that are performed under such condition that an aqueous solution of the monomer is used.

The concentration of the monomer contained in the aqueous solution (hereinafter, referred to as monomer aqueous solution) is determined depending on temperature of the aqueous solution and a type of the monomer, and is not particularly limited. However, the concentration of the monomer is preferably 10 to 70 mass %, more preferably 20 to 60 mass %. Further, in carrying out the aqueous solution polymerization, solvent other than water may be used together as required, and a type of the solvent used together is not particularly limited.

Note that, the reversed suspension polymerization is a polymerization method in which a monomer aqueous solution is suspended in a hydrophobic organic solvent, and is recited for example in U.S. Pat. No. 4,093,776, U.S. Pat. No. 4,367,323, U.S. Pat. No. 4,446,261, U.S. Pat. No. 4,683,274, U.S. Pat. No. 5,244,735, and the like. Further, the aqueous solution polymerization is a method in which the monomer aqueous solution is polymerized without using a dispersion solvent, and is recited for example in U.S. Pat. No. 4,625,001, U.S. Pat. No. 4,873,299, U.S. Pat. No. 4,286,082, U.S. Pat. No. 4,973,632, U.S. Pat. No. 4,985,518, U.S. Pat. No. 5,124,416, U.S. Pat. No. 5,250,640, U.S. Pat. No. 5,264,495, U.S. Pat. No. 5,145,906, U.S. Pat. No. 5,380,808, European Patent No. 0811636, European Patent No. 0955086, European Patent No. 0922717, European Patent No. 1178059, and the like. Monomers, initiators, and the like, that are used in these polymerization methods as examples are applicable to the present embodiment.

Further, in initiating the polymerization, it is possible to use: a radical polymerization initiator such as potassium persulfate, ammonium persulfate, sodium persulfate, t-butylhydroperoxide, hydrogen peroxide, 2,2'-azobis (2-amidino-propane) dihydrochloride; a photopolymerization initiator such as 2-hydroxy-2-methyl-1-phenyl0propane; or an active energy ray such as an ultraviolet ray and an electron ray. In terms of the properties, an amount of polymerization initiators used is ordinarily 0.001 to 2 mol %, preferably 0.01 to 0.1 mol % (with respect to all the monomers).

Further, in case of using an oxidizing radical polymerization initiator, redox polymerization may be carried out by using a reducer such as sodium sulfite, sodium bisulfite, ferrous sulfate, L-ascorbic acid, and the like, together. In terms of the properties, an amount of polymerization initiators used is ordinarily 0.001 to 2 mol %, preferably 0.01 to 0.1 mol % (with respect to all the monomers).

After the polymerization, the resultant is ordinarily a cross-linked polymer in an aqueous gel phase, and is dried as required. Ordinarily, the cross-linked polymer in the aqueous gel phase is pulverized before and/or after the drying, thereby obtaining the water absorbent resin (A). Further, the drying treatment is performed ordinarily at 60° C. to 250° C., preferably at 100° C. to 220° C., more preferably 120° C. to 200° C. The drying time depends on a surface area and a moisture content of the polymer and a type of the dryer, and is set so as to realize a desired moisture content.

The moisture content (defined by a moisture content found by measuring a drying loss after drying the water absorbent resin or the water absorbent resin composition that has been left at 180° C. for three hours) of the water absorbent resin or the water absorbent resin composition, whose surface has been or has not been cross-linked, which is used in the present embodiment, is not particularly limited. However, the moisture content is preferably 0.2 to 30 wt %, more preferably 0.3 to 15 wt %, further more preferably 0.5 to 10 wt % so that the water absorbent resin is in a powder phase, in terms of properties of the obtained water absorbent resin composition.

A particle shape of thus obtained water absorbent resin (A) whose surface has been or has not been cross-linked is not particularly limited such as a spherical shape or coagulum shape made up of spherical particles, a granular shape, an indeterminate shape, and the like. However, an indeterminate granular shape obtained through the pulverizing step is preferable. Further, its bulk density (defined by JIS K-3362) 0.40 to 0.80 g/ml, more preferably 0.50 to 0.75 g/ml, further preferably 0.60 to 0.73 g/ml in terms of superior properties of the water absorbent resin composition.

The water absorbent resin (A) in the present embodiment can be obtained by cross-linking a surface of a water absorbent resin, which has been subjected to the internal cross-linking process and the dry process, by using the organic surface cross-linking agent. The following description explains the organic surface cross-linking agent.

(II) Organic Surface Cross-Linking Agent (C)

There are various kinds of surface cross-linking agents for cross-linking the surface. For attaining better properties of the obtained water absorbent resin, it is general to use the following cross-linking agents: (a) polyol compounds, (b) epoxy compounds, (c) multivalent amine compounds, (d) condensates of the multivalent amine compounds and haloepoxy compounds, (e) oxazoline compounds, (f) mono, di, or poly oxazolidine compounds, (g) alkylene carbonate compounds, (h) cyclic urea compounds, (i) trimethylene oxide compounds, (j) and the like.

As the organic surface cross-linking agent used in the present embodiment, specific examples are given in U.S. Pat. No. 6,228,930, U.S. Pat. No. 6,071,976, U.S. Pat. No. 6,254, 990, and the like. Examples of the organic surface cross-linking agent (C) include: polyol compounds such as ethyleneglycol, diethyleneglycol, propyleneglycol, triethyleneglycol, tetraethyleneglycol, polyethyleneglycol, 1,3-propanediol, dipropyleneglycol, 2,2,4-trimethyl-1,3-pentandiol, polypropyleneglycol, glycerin, polyglycerin, 2-butene-1,4-diol, 1,3-butandiol, 1,4-butandiol, 1,5-pentandiol, 1,6-hexanediol, 1,2-cyclohexanedimethanol, 1,2-cyclohexanol, trimethylolpropane, diethanolamine, triethanolamine, polyoxypropylene, oxyethlene-oxypropylene block copolymer, pentaerythritol, and sorbitol; epoxy compounds such as ethyleneglycol diglycidyl ether, polyethylene glycidyl ether, glycerol polyglycidyl ether, diglycerol polyglycidyl ether, polyglycerol polyglycidyl ether, propyleneglycol diglycidyl ether, polypropyleneglycol diglycidyl ether, and glycidol; multivalent amine compounds such as ethylenediamine, diethylenetriamine, triethylenetetramine, tetraethylenepentamine, pentaethylenehexamine, and polyethyleneimine; multivalent isocyanate compounds such as 2,4-tolylenediisocyanate, and hexamethylenediisocyanate; multivalent oxazoline compounds such as 1,2-ethylenebisoxazoline; alkylene carbonate compounds such as 1,3-dioxolane-2-one, 4-methyl-1,3-dioxolane-2-one, 4,5-dimethyl-1, 3-dioxolane-2-one, 4,4-dimethyl-1,3-dioxolane-2-one, 4-ethyl-1,3-dioxolane-2-one, 4-hydroxymethyl-1,3-dioxolane-2-one, 1,3-dioxane-2-one, 4-methyl-1,3-dioxane-2-one, 4,6-dimethyl-1,3-dioxane-2-one, and 1,3-dioxisopane-2-one; haloepoxy compounds such as epichlorohydrin, epibromohydrin, and α-methylepichlorohydrin, and multivalent amine addition products thereof (for example, Kymene produced by Hercules: registered trademark); silane coupling agents such as γ-glycidoxypropyltrimethoxysilane and γ-aminopropyltriethoxysilane; and oxethane compounds such as 3-methyl-3-oxethane methanol, 3-ethyl-3-oxethane methanol, 3-butyl3-oxethane methanol, 3-methyl-3-oxethane ethanol, 3-ethyl-3-oxethane ethanol, 3-butyl-3-oxethane ethanol, 3-chloromethyl-3-methyloxethane, 3-chloromethyl-3-ethyloxethane, and a multivalent oxethane compound. Among the cross-linking agents, the multivalent alcohol is preferable since it is superior in terms of safety and it improves the hydrophilic property of the particle surface of the water absorbent resin. It is preferable that the multivalent alcohol contains 2 to 10 carbon atoms, preferably 3 to 8 carbon atoms. Among them, it is particularly preferable to use propyleneglycol, butandiol, glycerin, or trimethylpropane since it is possible to prevent a boundary tension from dropping and to prevent elution from dropping the liquid permeability.

The polyhydric alcohol reacts with the particulate water absorbent resin as the surface cross-linking agent so as to form an ester bond. Further, due to the reaction, some hydroxyl groups of the polyhydric alcohol do not react, so that the hydroxyl groups remain on the surface of the particulate water absorbent resin. Therefore, the hydroxyl groups, contained in the polyhydric alcohol, which do not react, improve the hydrophilic property on the surface of the particulate water absorbent resin.

An amount of the organic surface cross-linking agent (C) used depends on compounds used and a combination thereof, but is preferably 0.01 weight parts to 10 weight parts, more preferably 0.001 weight parts to 5 weight parts, with respect to 100 weight parts of the water absorbent resin. When the amount of the organic surface cross-linking agent (C) is less than 0.001 weight parts, the moisture absorption blocking property and the liquid permeability/liquid diffusing property are not sufficiently improved. When the amount of the organic surface cross-linking agent (C) is more than 10 weight parts, a centrifuge retention capacity (CRC), a diffusing absorbency under pressure (DAP), and an absorbency against pressure (AAP) significantly drop.

In the present embodiment, it is preferable to use water as a solvent in combination with the surface cross-linking agent in performing the surface cross-linking treatment. In this case, an amount of the water to be used depends on how much moisture content of the water absorbent resin to be used has. In general, with respect to 100 weight parts of the water absorbent resin, the amount of the water to be used is in a range of 0.5 weight parts to 20 weight parts, and preferably 0.5 weight parts to 5 weight parts. Further, in the present embodiment, it is possible to use a hydrophilic organic solvent other than water. An amount of the hydrophilic organic solvent is in a range of 0 weight part to 10 weight parts, preferably in a range of 0 weight part to 5 weight parts, and more preferably in a range of 0 weight part to 3 weight parts with respect to 100 weight parts of the water absorbent resin.

Various methods can be adopted in adding the surface cross-linking agent, but the following mixing method is preferable: in advance, the surface cross-linking agent is mixed with water and/or the hydrophilic organic solvent as required, and the mixture is sprayed or dropped directly to the water absorbent resin. It is more preferable to spray the mixture directly to the water absorbent resin. An average diameter of liquid droplets to be sprayed is preferably 300 μm or less, and more preferably 200 μm or less. In adding the surface cross-linking agent, it may be so arranged that a water-insoluble fine particle powder and a surfactant are made to coexist so that they do not prevent effects of the present invention.

After mixing the surface cross-linking agent with the water absorbent resin, it is preferable that the water absorbent resin is subjected to a thermal treatment. Conditions of the thermal treatment are as follows: a heating temperature is in a range of 100° C. to 250° C., more preferably in a range of 150° C. to 250° C.; and a heating time is preferably in a range of one minute to two hours. Examples of appropriate combinations of the heating temperature and heating time are: (a) 180° C. for 0.1 to 1.5 hours, and (b) 200° C. for 0.1 to one hour.

The water absorbent resin composition of the present embodiment is obtained by adding and mixing a solution of the water-soluble multivalent metal compound (B) to the particulate water absorbent resin (A) obtained in the foregoing manner.

(III) Multivalent Metal Compound (B) and Multivalent Metal Component

The multivalent metal compound (B) of the present embodiment is a compound having bivalent or further multivalent metal atoms. Further, the multivalent metal component of the present embodiment is constituted of bivalent or further multivalent metal atoms contained in the multivalent metal compound (B). For example, aluminum sulfate ($Al_2(SO_4)_3$) is a compound including aluminum (Al) which has tervalent atoms, so that the aluminum sulfate is the multivalent metal compound (B), and aluminum (Al) constituted of tervalent metal atoms contained in the multivalent metal compound is the multivalent metal component.

Further, it is preferable that the multivalent metal component used in the present invention includes one or more metals selected from typical metals and transition metals whose group numbers are 4 to 12. Among the multivalent metal components, it is more preferable that the multivalent metal compound (B) includes Mg, Ca, Ti, Zr, V, Cr, Mn, Fe, Co, Ni, Pd, Cu, Ag, Zn, Cd, and Al. Al is particularly preferable. It is preferable that the multivalent metal compound (B) is water-soluble. The "water-soluble" of the present invention means a condition under which 1 g or more, preferably 10 g or more, of a compound dissolves in 100 g of water whose temperature is 25° C.

Examples of the multivalent metal compound (B) which can be used in the present embodiment include: aluminum chloride, polyaluminum chloride, aluminum sulfate, aluminum nitrate, bis aluminum potassium sulfate, bis aluminum sodium sulfate, calcium chloride, calcium nitrate, magnesium chloride, magnesium sulfate, magnesium nitrate, zinc chloride, zinc sulfate, zinc nitrate, copper sulfate, cobalt chloride, zirconium chloride, zirconium sulfate, and zirconium nitrate. Further, in terms of solubility, it is preferable to use salt having these crystal waters. It is particularly preferable to use aluminum compounds. Among of them, it is preferable to use aluminum sulfate, and it is possible to most favorably use powder of hydrated crystal such as aluminum sulfate octadecahydrate and aluminum sulfate hydrate (tetradecahydrate to octadecahydrate). Further, two or more kinds of the aforementioned compounds may be used.

(IV) Water Absorbent Resin Composition

The water absorbent resin composition according to the present embodiment is a water absorbent resin composition, whose main component is a particulate water absorbent resin (A) having a cross-linking structure obtained by polymerizing an unsaturated monomer containing an acid radical, said particulate water absorbent resin (A) being cross-linked in a vicinity of a surface of the water absorbent resin (A), wherein: the water absorbent resin composition contains 95 wt % or more of particles whose particle diameter is less than 850 μm and not less than 106 μm, and a weight average particle diameter of the particles is less than 500 μm and not less than 300 μm, and a logarithmic standard deviation (σζ) of a particle size distribution of the water absorbent resin composition is 0.45 or less, and a water-soluble component of the water absorbent composition is 35 wt % or less, and the water absorbent resin composition includes a multivalent metal component, and an extraction rate of the multivalent metal component is 5.0 wt % or more and less than 100 wt %.

As to the particle diameter of the particulate water absorbent resin (A) of the present embodiment, it is preferable that the average particle diameter is 300 μm or more and 500 μm or less. When the average particle diameter is less than 300 μm, the moisture absorption blocking ratio is raised at the time of water absorption, so that the gel blocking tends to occur. Further, when the average particle diameter exceeds 500 μm, an absorption rate (Vortex) becomes low. Thus, when the water absorbent resin composition according to the present embodiment is used in the absorber and/or the absorbent article such as a paper diaper, this results in problems such as liquid leakage and skin fit.

Further, the particulate water absorbent resin (A) contains 95 to 100 wt %, preferably 97 to 100 wt %, more preferably 99 to 100 wt % of particles whose particle diameter is less than 850 μm and not less than 106 μm, and a logarithmic standard deviation (σζ) of its particle size distribution is 0.45 or less, preferably 0.40 or less, more preferably 0.35 or less, most preferably 0.30 or less. Further, it is preferable that the logarithmic standard deviation (σζ) is 0.20 or more. As the logarithmic standard deviation (σζ) of the particle size distribution is smaller, the particle size distribution is narrower.

Note that, when the amount of the particles whose particle diameter is less than 850 μm and not less than 106 μm is less than 95 wt % with respect to the whole particulate water absorbent resin (A), a large number of particles whose particle diameter is not less than 850 μm and a large number of particles whose particle diameter is less than 106 μm are contained in the water absorbent resin. When a large number of particles whose particle diameter is not less than 850 μm are contained in the particulate water absorbent resin (A), the particulate water absorbent resin (A) feels grainy in a sanitary material such as a diaper. When a large number of particles whose particle diameter is less than 106 μm are contained in the particulate water absorbent resin (A), the particulate water absorbent resin (A) may pass through a surface material (referred to also as a top sheet or liquid permeation sheet) of the sanitary material such as the diaper. Thus, the use of such water absorbent resin is not preferable. Further, when the logarithmic standard deviation (σζ) of the particle size distribution is less than 0.20, the productivity significantly drops, so that it may be impossible to obtain an effect corresponding to the cost. When the logarithmic standard deviation (σζ) of the particle size distribution exceeds 0.45, the particle size distribution is excessively widened, so that it may be impossible to obtain the desired moisture absorption blocking property and the desired liquid permeation/liquid diffusing property. Thus, the use of such water absorbent resin is not preferable.

The foregoing particle diameter is applied also to a water absorbent resin composition described later. That is, the water absorbent resin composition according to the present embodiment includes 95 to 100 wt %, preferably 97 to 100 wt %, more preferably 99 to 100 wt % of particles whose particle diameter is less than 850 μm and more than 106 μm or less, with respect to the whole water absorbent resin composition, and a logarithmic standard deviation (σζ) of a particle size distribution is 0.45 or less, preferably 0.40 or less, more preferably 0.35 or less, most preferably 0.30 or less. Further, it is preferable that the logarithmic standard deviation (σζ) of the particle size distribution is 0.20 or more. Further, the particle diameter of the water absorbent resin or the water absorbent resin composition may be adjusted by agglomeration or the like as required.

Further, the gel blocking and the moisture absorption blocking are influenced by the water-soluble component of the particulate water absorbent resin. In the present embodiment, the amount of the water-soluble component is 5 wt % or more and 35 wt % or less, preferably 5 wt % or more and 25 wt % or less, more preferably 5 wt % or more and 20 wt % or less, particularly preferably 5 wt % or more and 15 wt % or less, and most preferably 5 wt % or more and 10 wt % or less. When the amount of the water-soluble component exceeds 35 wt %, the water-soluble component of the particulate water absorbent resin elutes at the time of water absorption. As a result, the water-soluble component functions like a binder between particles in the particulate water absorbent resin, so that the gel blocking tends to occur. Thus, the use of such water absorbent resin is not preferable. Further, when the water-soluble component is less than 5 wt %, the productivity of the water absorbent resin composition significantly drops, and the production cost significantly rises, so that such arrangement is not preferable.

Further, the water-soluble component can be applied also to the water absorbent resin composition according to the present embodiment. That is, in the present embodiment, the water-soluble component of the water absorbent resin composition is 5 wt % or more and 35 wt % or less, preferably 5 wt % or more and 25 wt % or less, more preferably 5 wt % or more and 20 wt % or less, particularly preferably 5 wt % or more and 15 wt % or less, most preferably 5 wt % or more and 10 wt % or less. When the water-soluble component exceeds 35 wt %, the water-soluble component of the particulate water absorbent resin elutes at the time of water absorption. As a result, the water-soluble component functions like a binder between particles in the particulate water absorbent resin, so that the gel blocking tends to occur. Thus, the use of such water absorbent resin is not preferable.

An amount of the particulate water absorbent resin (A) contained in the water absorbent resin composition as a main component is 70 wt % or more and less than 100 wt %, preferably 80 wt % or more and less than 100 wt %, further more preferably 90 wt % or more and less than 100 wt %, most preferably 95 wt % or more and less than 100 wt %, with respect to the water absorbent resin composition.

Further, the inventors of the present invention found that: as to the water absorbent resin composition of the present embodiment, it is important that the multivalent metal component exists in a vicinity of a surface of the particulate water absorbent resin subjected to the surface treatment. Further, it is possible to specify the multivalent metal component, which exists in a vicinity of a surface of the water absorbent resin particles, in accordance with an extraction rate of the multivalent metal component (the extraction rate will be described in Examples).

In order to improve the moisture absorption blocking property in high humidity and realize an extremely superior liquid permeation/liquid diffusing property while preventing the centrifuge retention capacity (CRC), the diffusing absorbency under pressure (DAP), and the absorbency against pressure (AAP) from dropping, the extraction rate of the multivalent metal component is 5.0 wt % or more and less than 100 wt %, preferably 8.0 wt % or more and 90.0 wt % or less, more preferably 10.0 wt % or more and 70.0 wt % or less.

The extraction rate of the multivalent metal component is 100 wt % in case where the multivalent metal component is mixed with the water absorbent resin in accordance with dry blending treatment. When the extraction rate of the multivalent metal component is too high, it is impossible to evenly mix the multivalent metal compound with a surface of the water absorbent resin, so that the moisture absorption blocking property in high humidity cannot be improved. Further, in case where the extraction rate of the multivalent metal component is less than 5.0%, the multivalent metal component penetrates into the water absorbent resin. This drops the centrifuge retention capacity (CRC), the diffusing absorbency under pressure (DAP), and/or the absorbency against pressure (AAP). Further, it is impossible to realize such improvement of the moisture absorption blocking property in high humidity that corresponds to the cost, and it is impossible to improve the liquid permeation/liquid diffusing property.

The moisture absorption blocking property of the water absorbent resin composition of the present embodiment is represented by the moisture absorption blocking ratio. The moisture absorption blocking ratio is measured by a known method. A specific example of the method for measuring the moisture absorption blocking ratio is as follows: as described in later Examples, a particulate water absorbent resin (or a water absorbent resin composition) is evenly dispersed on a bottom of a predetermined cup, and the water absorbent resin which has absorbed moisture at 25° C. with a relative humidity of 90% for one hour is sieved for a certain time by a sieve shaker, and the moisture absorption blocking ratio is measured on the basis of a weight W4 (g) of the water absorbent resin which remains on the sieve and a weight W5 (g) of the water absorbent resin which passed through the sieve.

Further, more specific examples of the method for measuring the moisture absorption blocking ratio are: (a) a method in which an aluminum cup (Foil Container, Product No. 107, Product of TOYO ECKO Inc.) whose bottom diameter is 52 mm and height is 22 mm is used as the predetermined cup and the water absorbent resin is sieved for 8 seconds by the sieve shaker so as to measure a moisture absorption blocking ratio (wt %) (hereinafter, referred to as a moisture absorption blocking ratio a); (b) a method in which a polypropylene cup whose bottom diameter is 50 mm and height is 10 mm is used as the predetermined cup and the water absorbent resin is sieved for five minutes by the sieve shaker so as to measure a moisture absorption blocking ratio (wt %) (hereinafter, referred to as a moisture absorption blocking ratio b); and a similar method.

In case where the moisture absorption blocking ratio a is measured in accordance with the method (a), the moisture absorption blocking ratio a is 0 wt % or more and 30 wt % or less, preferably o wt % or more and 20 wt % or less, more preferably 0 wt % or more and 10 wt % or less, most preferably 0 wt % or more and 5 wt % or less, under such condition that the water absorbent resin is left at 25° C. with a relative humidity of 90% for one hour. When the moisture absorption blocking ratio a exceeds 30 wt %, it is difficult to handle the water absorbent resin composition in high humidity. This condition may cause such problem that: in a production plant, the water absorbent resin composition and/or the water absorbent resin particle are coagulated and jammed in a transportation pipe, and it is impossible to evenly mix them with a hydrophilic fiber, at the time of production of a thin absorber used in a sanitary material described later.

In case where the moisture absorption blocking ratio b is measured in accordance with the method (b), the moisture absorption blocking ratio a is 0 wt % or more and 40 wt % or less, preferably 0 wt % or more and 30 wt % or less, more preferably 0 wt % or more and 20 wt % or less, most preferably 0 wt % or more and 10 wt % or less, under such condition that the water absorbent resin is left at 25° C. with a relative humidity of 90% for one hour. When the moisture absorption blocking ratio a exceeds 40 wt %, it is difficult to handle the water absorbent resin composition in high humidity. This condition may cause such problem that: in a production plant, the water absorbent resin composition and/or the water absorbent resin particle are coagulated and jammed in a transportation pipe, and it is impossible to evenly mix them with a hydrophilic fiber, at the time of production of a thin absorber used in a sanitary material described later.

Further, the liquid permeability and the liquid diffusing property of the water absorbent resin composition of the present embodiment are represented by a saline flow conductivity (SFC: a barometer indicative of a liquid permeation rate under pressure) mentioned in Published Japanese Translations of International Publication of Patent Application No. 509591/1997 (Tokuhyohei 9-509591). The saline flow conductivity (SFC) is preferably $30 \times 10^{-7}$ cm$^3$·s/g or more, more preferably $70 \times 10^{-7}$ cm$^3$·s/g, further more preferably $100 \times 10^{-7}$ cm$^3$·s/g, particularly preferably $120 \times 10^{-7}$ cm$^3$·s/g, most preferably $140 \times 10^{-7}$ cm$^3$·s/g.

As to the water absorbent resin composition according to the present invention, its centrifuge retention capacity (CRC) at which 0.90 wt % of saline is absorbed for 30 minutes without any load is preferably 25 g/g or more and 50 g/g or less, more preferably 27 g/g or more and 45 g/g or less, further more preferably 28 g/g or more and 40 g/g or less, particularly preferably 29 g/g or more and 38 g/g or less, most preferably 30 g/g or more and 35 g/g or less. When the CRC is less than 25 g/g, a liquid-absorbing ability of the water absorbent resin composition deteriorates. Thus, when the water absorbent resin composition according to the present embodiment is used in the absorber and/or the absorbent article such as a paper diaper, this results in problems such as a liquid leakage and a skin rash. The use of such water absorbent resin composition is not preferable. Further, there is a case where a load such as a weight of a wearer of a paper diaper is exerted to the absorber and/or the absorbent article in practically using the water absorbent resin composition in the paper diaper or the like. Further, when CRC exceeds 50 g/g, an amount of the water-soluble component of the particulate water absorbent resin is large. Thus, the particulate water absorbent resin causes the gel blocking, so that it may be impossible to obtain the desired liquid permeation/liquid diffusing property. The use of such water absorbent resin is not preferable.

Further, the absorbency against pressure (AAP) at which 0.90 wt % of saline is absorbed for an hour under pressure of 0.7 psi (4.83 kPa) is preferably 20 g/g or more, more preferably 21 g/g or more and 50 g/g or less, further more preferably 23 g/g or more and 40 g/g or less, particularly preferably 25 g/g and 30 g/g or less. In practically using the water absorbent resin composition in a paper diaper or the like, a weight of the user wearing the paper diaper is sometimes exerted to the absorber and/or the absorbent article. In case where the absorbent against pressure (AAP) is less than 20 g/g, when a load such as a weight is exerted to the water absorbent resin composition, an absorbing ability for liquid such as urine deteriorates. This may result in problems such as a liquid leakage and a skin rash in practically using the water absorbent resin composition in the paper diaper.

Further, a diffusing absorbency under pressure (DAP) at which 0.90 mass % of physiological saline is absorbed for 60 minutes under pressure of 1.9 kPa is 20 g/g or more and 50 g/g or less, preferably 24 g/g or more and 45 g/g or less, more preferably 28 g/g or more, most preferably 32 g/g or more and 40 g/g or less. In the case where the diffusing absorbency under pressure (DAP) is less than 20 g/g, when a load such as a weight is exerted to the water absorbent resin composition, a liquid diffusing ability and an absorbing ability for liquid such as urine are deteriorated. Thus, the liquid is not diffused in the absorber and/or the absorbent article and a blocking phenomenon occurs in the liquid. Under such condition, the liquid does not spread over the water absorbent resin composition used. This may result in problems such as a liquid leakage and a skin rash in practically using the water absorbent resin composition in the paper diaper. The use of such water absorbent resin is not preferable.

Further, the shape, the solid content (moisture content), and the water-soluble component of the water absorbent resin composition of the present embodiment are in the aforementioned ranges, and the amount of the water-soluble component is preferably 25 wt % or less, more preferably 20 wt % or less, further more preferably 15 wt % or less. Further, the concentration of the remaining monomer is 0 to 400 ppm, and more preferably 0 to 300 ppm.

The water absorbent resin composition of the present embodiment is used in sanitary materials such as sanitary napkins, incontinence pads, medical pads, and the like. In this case, it is preferable to arrange such sanitary material that includes (a) a liquid permeable top sheet disposed adjacent to a body of the user, (b) a liquid impermeable back sheet disposed adjacent to a clothe of the user so as to be away from the body of the user, and (c) an absorber disposed between the top sheet and the back sheet. The absorber may be arranged so as to be two-or-more-layered, or may be used with a pulp layer. The absorber is an absorbent layer in which a fiber base material or the like is included as required.

The water absorbent resin composition of the present embodiment is free from any coagulation of particles even in high humidity, and exhibits a superior liquid permeation/liquid diffusing property. The water absorbent resin composition exhibits a superior moisture absorption blocking property. Thus, it is possible to produce the sanitary material, without any trouble such as adhesion to a pipe and/or plug in the pipe, at the time of production of the absorber even in high humidity. The water absorbent resin composition is superior also in the liquid permeation/liquid diffusing property. Thus, compared with conventional ones, the absorber of the present embodiment includes a large amount (high core concentration) of the water absorbent resin composition with respect to a total weight of the water absorbent resin composition and the hydrophilic fiber. As a result, it is possible to produce an extremely thin sanitary material.

An amount (core concentration) of the contained water absorbent resin composition with respect to a total amount of the water absorbent resin composition and the hydrophilic fiber is preferably 20 to 100 mass %, more preferably 30 to 90 mass %, most preferably 40 to 80 mass %. In this manner, when the water absorbent resin composition of the present embodiment is used, it is possible to produce a thin absorber superior in the absorbent property without any trouble at the time of production. The thin absorber is sandwiched by a liquid-permeable base material (surface sheet) and a liquid-impermeable base material (back sheet), and is provided with an elastic member, a diffusion layer, an adhesive tape, and the like, thereby obtaining an absorbent article (product for consumers), particularly an adult paper diaper and a sanitary napkin. The absorber is pressed so that its density is 0.06 to 0.50 g/cc and its basic weight is 0.01 to 0.20 g/cm$^2$. Note that, the fiber base material used is a hydrophilic fiber, for example, crushed wood pulp, a cotton linter, a cross-linked cellulose fiber, rayon, cotton, wool, acetate, or vinylon. These fiber base materials are preferably aerated.

As described above, the water absorbent resin composition of the present embodiment is obtained by (i) adding an aqueous solution of a water-soluble multivalent metal compound having a specific solution concentration to the particulate water absorbent resin (A), having a specific particle size distribution, whose surface vicinity has been cross-linked, and (ii) mixing them with each other. Note that, according to conventional techniques such as (1) a method in which powdery multivalent metal salt is dry-blended with a water absorbent resin, (2) a method in which a multivalent metal salt is dry-blended with a water absorbent resin and water or the like is, dropped and mixed with thus obtained mixture, (3) a method in which a surface cross-linking agent of a water absorbent resin and an aqueous solution of a multivalent metal salt are simultaneously added and mixed so that the concentration of the multivalent metal component is less than 1.80 weight parts (%) and is then heated, and a similar method, it is impossible to obtain the water absorbent resin composition of the present embodiment which has a specific extraction rate of the multivalent metal component.

The following description is speculation concerning these methods. In case of the method (1), the extraction rate of the multivalent metal component is substantially 100%, and the multivalent metal salt is dry-blended, so that it is impossible to evenly mix the multivalent metal component with a surface of the water absorbent resin. As a result, the moisture absorption blocking property is not improved. In case of the method (2), as in the method (1), it is impossible to evenly coat the surface of the water absorbent resin at the time of dry-blending of the multivalent metal salt, and water is added under such condition, so that the water is quickly absorbed by a part of the water absorbent resin particles. Thus, the multivalent metal salt may permeate the water absorbent resin. As a result, the moisture absorption blocking property is not improved, and the centrifuge retention capacity (CRC), the diffusing absorbency under pressure (DAP), and the absorbency against pressure (AAP) may drop. Further, in case of the method (3), the moisture absorption blocking property is not improved. This may be based on the following reason: according to such a method that the surface cross-linking agent and the aqueous solution of the multivalent metal salt are simultaneously added, mixed, and heated, a ratio of the multivalent metal component which exists in a vicinity of the surface of the water absorbent resin so as to improve the moisture absorption blocking property becomes smaller.

(V) Production Method of the Water Absorbent Resin Composition

It is important that a surface of the water absorbent resin composition of the present embodiment is evenly coated with the multivalent metal component while preventing the multivalent metal component from permeating the water absorbent resin. In order to evenly coat the surface of the water absorbent resin with the solution of the multivalent metal compound (B), it is important that a vicinity of the surface of the particulate water absorbent resin is cross-linked and its particle size distribution is specified as described above. The inventors of the present invention found this, thereby devising the present invention. Further, the inventors found it possible to evenly provide the multivalent metal component in the vicinity of the surface of the water absorbent resin while preventing the multivalent metal component from permeating the water absorbent resin by adjusting the solution concentration of the multivalent metal compound (B) to the aforementioned specific range, thereby devising the present invention.

That is, it is possible to obtain the water absorbent resin composition according to the present embodiment by adding a solution of the aqueous multivalent metal compound (B) to the particulate water absorbent resin (A) and mixing them with each other. Note that, in the present embodiment, the solution is regarded as a solution of the aqueous multivalent metal compound (B) as long as the multivalent metal compound (B) dissolves even though the concentration of the multivalent metal compound (B) exceeds a saturation concentration and a part of the multivalent metal compound (B) is precipitated or dispersed.

Further, an amount of the multivalent metal compound (B) used varies depending on the desired moisture absorption blocking property and the desired liquid permeation/liquid diffusing property. However, the amount of the multivalent metal compound (B) added as the multivalent metal component is preferably 0.001 to 10 weight parts, more preferably 0.01 to 5 weight parts, particularly preferably 0.05 to 1 weight parts, with respect to 100 weight parts of a solid content. In case where the multivalent metal component is less than 0.001 weight parts, the moisture absorption blocking property and the liquid permeation/liquid diffusing property are not sufficiently improved. In case where the multivalent metal component exceeds 100 weight parts, the centrifuge retention capacity (CRC), the diffusing absorbency under pressure (DAP), and the absorbency against pressure (AAP) significantly drop. As a result, it is impossible to obtain effects corresponding to the amount of the multivalent metal compound (B) added.

Further, in the method according to the present embodiment for producing the water absorbent resin composition, as the solution of the multivalent metal compound (B), it is possible to use a solution obtained by dissolving the multivalent metal compound (B) in water and/or aqueous solution or various kinds of hydrophilic organic solvent, but it is preferable to use an aqueous solution. A suitable amount of a solvent, i.e., water, vapor, or an aqueous liquid constituted of water and hydrophilic organic solvent, with respect to solid contents of the water absorbent resin varies depending on a type and a particle size of the water absorbent resin. However, generally, in case where the solvent is water, the suitable amount thereof is more than 0 to 10 weight parts or less, preferably 1 to 5 weight parts, with respect to 100 weight parts of solid contents. Likewise, an amount of the hydrophilic organic solvent used is generally 0 to 10 weight parts or less, preferably 0.1 to 5 weight parts, with respect to 100 weight parts of the solid contents.

The solution concentration of the multivalent metal compound (B) used is adjusted so that a ratio of the aqueous solution concentration and the saturation concentration at 25° C. is 0.40 or more, preferably 0.50 or more, more preferably 0.60, most preferably 0.70 or more, so that it is possible to improve the moisture absorption blocking property in high humidity and to prevent the centrifuge retention capacity (CRC), the diffusing absorbency under pressure (DAP), and the absorbency against pressure (AAP) from dropping. The inventors of the present invention first found this. As a result, they devised the present invention. Note that, the concentration of the aqueous solution added may exceed the saturation concentration at 25° C. That is, generally, an upper limit of a ratio of the concentration of the added aqueous solution with respect to the saturation concentration is preferably 1.50 or less, more preferably 1.00 or less. When the ratio of the aqueous solution concentration and the saturation concentration is less than 0.40, the multivalent metal component permeates the water absorbent resin, so that the centrifuge retention capacity (CRC), the diffusing absorbency under pressure (DAP), and the absorbency against pressure (AAP) drop, and the multivalent metal component influence the improvement of the moisture absorption blocking property in high humidity. Thus, an amount of the multivalent metal component existing in a vicinity of a surface of the water absorbent resin becomes smaller. This may be a reason for which it is impossible to realize such improvement of the moisture absorption blocking property that corresponds to the amount of the solution of the multivalent metal component.

Further, in adding the solution of the aqueous multivalent metal compound to the particulate water absorbent resin (A) which has been subjected to the surface cross-linking treatment, temperature of the particulate water absorbent resin (A) is preferably 50° C. or higher and lower than 100° C., more preferably 50° C. or higher and lower than 80° C., further preferably 50° C. or higher and lower than 70° C. When the temperature of the particulate water absorbent resin (A) is lower than 50° C., moisture of the solution of the multivalent metal compound less vaporizes after the solution of the multivalent metal compound is added to the particulate water absorbent resin (A). Thus, when the temperature of the particulate water absorbent resin (A) is lower than 50° C., the multivalent metal component permeates the particulate water absorbent resin (A). As a result, it is impossible to realize such improvement of the moisture absorption blocking property that corresponds to the amount of the multivalent metal component added. Such arrangement is not preferable. Further, when the temperature of the particulate water absorbent resin (A) exceeds 100° C., the particulate water absorbent resin (A) and the multivalent metal component are unevenly mixed, or the particulate water absorbent resin deteriorates. Thus, such arrangement is not preferable.

Further, when a temperature of the solution of the aqueous multivalent metal compound is higher, it is possible to raise the concentration of the multivalent metal component contained in the solution. Thus, a larger amount of the multivalent metal component can exist on the surface of the water absorbent resin. Temperature of the aqueous solution of the multivalent metal compound is preferably 30° C. or higher and lower than 100° C., more preferably 50° C. or higher and lower than 100° C., further more preferably 70° C. or higher and lower than 100° C. When the temperature of the aqueous solution of the multivalent metal compound is lower than 30° C., the concentration of the multivalent metal component of the solution of the multivalent metal compound becomes lower, so that the multivalent metal component permeates the particulate water absorbent resin. As a result, it is impossible to realize such improvement of the moisture absorption blocking property that corresponds to the amount of the multivalent metal component added. Such arrangement is not preferable. Further, when the temperature of the aqueous solution of the multivalent metal compound exceeds 100° C., the particulate water absorbent resin (A) deteriorates, so that it is impossible to realize such sufficient improvement of the moisture absorption blocking property that corresponds to the amount of the multivalent metal component added. Thus, such arrangement is not preferable.

In the present invention, examples of a device which adds and mixes the aqueous solution of the multivalent metal compound (B) with the particulate water absorbent resin (A) are as follows: a cylindrical mixer, a screw mixer, a screw extruder, a turbulizer, a nauta mixer, a V-shaped mixer, a ribbon blender, a double-arm kneader, a flow mixer, an air current mixer, a rotary disc mixer, a roll mixer, a convolution mixer, and a Lödige mixer. A mixing speed is not particularly limited to a high speed or a low speed.

After mixing the multivalent metal compound (B), a heating process and classification may be performed as required. Further, it may be so arranged that: temperature thereof is adjusted during or after addition/mixing of the multivalent metal compound (B), thereby controlling the precipitation and dispersion of the multivalent metal component.

The water absorbent resin and the water absorbent resin composition according to the present embodiment may be, where necessary, subjected to another step of adding various additives. Examples of the additives include: deodorant; antibacterial agent; perfume; foaming agent; pigment; dye; plasticizer; adhesive; surfactant; fertilizer; oxidizing agent; reducing agent; water; salt; chelating agent; bactericide; hydrophilic polymer, such as polyethylene glycol, and polyethyleneimine; hydrophobic polymer, such as paraffin; thermoplastic resins, such as polyethylene and polypropylene; and thermosetting resins, such as a polyester resin and urea resin. The additives are added at quantities from 0 to 20 wt %, preferably from 0 to 5 wt %, more preferably 0 to 1 wt %, with respect to the water absorbent resin composition.

Embodiment 2

A water absorbent resin composition according to the present embodiment includes a particulate water absorbent resin (A) and a multivalent metal component (B) that are similar to those of Embodiment 1. However, in the present embodiment, a particulate water absorbent resin (A) having a cross-linking structure obtained by polymerizing an unsaturated monomer containing an acid group, a solution of an aqueous multivalent metal compound (B), and an organic surface cross-linking agent (C) are mixed with each other, thereby obtaining the water absorbent resin composition. The following description explains a method according to the present embodiment for producing the water absorbent resin composition.

(IV) Production Method of the Water Absorbent Resin of the Present Embodiment

The water absorbent resin composition of the present embodiment can be obtained by heating a mixture of the particulate water absorbent resin (A), the solution of the multivalent metal compound (B), and the organic surface cross-linking agent (C), at 150 to 300° C. However, a method for mixing the particulate water absorbent resin (A), the solution of the multivalent metal compound (B), and the organic surface cross-linking agent (C) with each other is not particularly limited. For example, it may be so arranged that the solution of the multivalent metal compound (B) and the organic surface cross-linking agent (C) are separately or simultaneously mixed with the particulate water absorbent resin (A), or it may be so arranged that a mixture solution obtained by mixing the solution of the multivalent metal compound (B) with the organic surface cross-linking agent (C) is mixed with the particulate water absorbent resin (A). It is preferable to adopt the method in which a mixture solution obtained by mixing the solution of the multivalent metal compound (B) with the organic surface cross-linking agent (C) is mixed with the particulate water absorbent resin (A). Note that, in the present embodiment, any solution is used as the "solution of the multivalent metal compound (B)" as long as 10 wt % or more of water is contained in the solution even when an organic solvent is contained.

Further, in mixing the organic surface cross-linking agent with the particulate water absorbent resin (A), inorganic acids, organic acids, polyamino acids that are mentioned in European Patent No. 0668080 may be introduced as a mixing coadjuvant. The mixing coadjuvant may function as a surface cross-linking agent. However, it is preferable to use a mixing coadjuvant which prevents the water absorbent property of the water absorbent resin from dropping after the surface is cross-linked. Particularly, it is preferable to use volatile alcohols whose boiling point is lower than 150° C. since the volatile alcohols vaporize so that there is no residue at the time of the surface cross-linking treatment. Further, in order to more evenly mix the organic surface cross-linking agent with the particulate water absorbent resin (A), it may be so arranged that: non-cross-linking water-soluble inorganic bases (preferably, alkali metal salt, ammonium salt, alkaline metal hydroxide, and ammonia or hydroxide thereof) and a non-reducing alkali metal salt pH buffer (preferably, hydrogen carbonate, dihydrogen salt phosphate, hydrogen salt phosphate, and the like) are made to coexist in mixing the water absorbent resin particles with the surface cross-linking agent. An amount of them varies depending on a kind and a particle size of the water absorbent resin particles, but is preferably 0.005 to 10 weight parts, more preferably 0.05 to 5 weight parts, with respect to 100 weight parts of the solid contents of the water absorbent resin particles.

In the present embodiment, a total amount of the organic surface cross-linking agent (C) and the multivalent metal compound (B) varies depending on respective amounts of the organic surface cross-linking agent (C) and the multivalent metal compound (B), but is preferably 0.001 weight parts to 10 weight parts, more preferably 0.01 weight parts to 5 weight parts, with respect to 100 weight parts of the water absorbent resin. When the total amount of the organic surface cross-linking agent (C) and the multivalent metal compound (B) is less than 0.001 weight parts, the moisture absorption blocking property and the liquid permeability/liquid diffusing property are not sufficiently improved. When the total amount of the organic surface cross-linking agent (C) and the multivalent metal compound (B) is not less than 10 weight parts, the centrifuge retention capacity (CRC), the diffusing absorbency under pressure (DAP), and the absorbency against pressure (AAP) significantly drop.

In order that the water absorbent resin compound of the present embodiment realizes both the superior moisture absorption blocking property and the superior liquid permeability/liquid diffusing property under a condition of high humidity, it is necessary that: concentration of the multivalent metal component in the aqueous solution in mixing the particulate water absorbent resin (A) with the solution of the multivalent metal compound (B) is at least 1.80 wt %, and the mixture of the particulate water absorbent resin (A), the organic surface cross-linking agent (C), and the solution of the multivalent metal compound (B) is heated at 150° C. to 300° C. This was found by the inventors of the present invention for the first time. As a result, the present invention was devised.

Unexpectedly, the inventors found that: a saline flow conductivity (SFC: a barometer indicative of a liquid permeation rate under pressure) of a water absorbent resin subjected to surface treatment with a surface treatment agent having a highly concentrated multivalent metal component is much higher than that of a water absorbent resin subjected to surface treatment with a surface treatment agent having a known concentration.

The solution of the highly concentrated multivalent metal compound (B) (at least 1.80 wt % of the multivalent metal component is contained in the aqueous solution) is mixed with the particulate water absorbent resin, so that the multivalent metal component exists around a surface layer of the water absorbent resin after preparing the mixture. As a result, the moisture absorption blocking property and the liquid permeation/liquid diffusing property are remarkably improved.

Note that, in the present embodiment, neither the solution prepared by mixing the particulate water absorbent resin (A) with the multivalent metal compound (B) nor the mixing method of the solution and the organic surface cross-linking agent (C) are particularly limited. For example, it is possible to adopt the following methods: (i) a solution of the multivalent metal compound (B) and the organic surface cross-linking agent (C) are separately or simultaneously mixed with the particulate water absorbent resin (A); and (ii) a mixture solution prepared by mixing the solution of the multivalent metal compound (B) with the organic surface cross-linking agent (C) is mixed with the particulate water absorbent resin (A). The "concentration (S/T-[M]) of the multivalent metal component contained in the solution of the multivalent metal compound (B)" in the methods (i) and (ii) is calculated in accordance with the following equations.

$$S/T\text{-}[M]\ (wt\%) \text{ in the method } (i) = \text{weight (g) of the multivalent metal component/weight (g) of the solution of the multivalent metal compound } (B) \times 100$$

$$S/T\text{-}[M]\ (wt\%) \text{ in the method } (ii) = \text{weight (g) of the multivalent metal component/(weight (g) of the solution of the multivalent metal compound } (B) + \text{weight (g) of the organic surface cross-linking agent } (C)) \times 100$$

The concentration of the multivalent metal component contained in the solution of the multivalent metal compound (B) used in the present embodiment is preferably 1.80 wt % or more, more preferably 2.00 wt % or more, further more preferably 2.50 wt % or more, most preferably 2.90 wt % or more.

In case where the concentration of the multivalent metal component contained in the aqueous solution of the multivalent metal compound (B) is less than 1.80 wt %, the multivalent metal component permeates the water absorbent resin, so that a smaller amount of the multivalent metal component exists in a vicinity of a surface of the water absorbent resin. Thus, it is impossible to realize such sufficient improvement of the moisture absorption blocking property and the liquid permeation/liquid diffusing property that corresponds to an amount of the multivalent metal component added. Further, an upper limit of the concentration of the multivalent metal component included in the solution of the multivalent metal compound (B) is not particularly limited, but is preferably 20 wt % or less, more preferably 10 wt % or less.

An amount of the multivalent metal compound (B) used varies depending on the desired moisture absorption blocking property and the desired liquid permeation/liquid diffusing property, but is preferably 0.001 weight parts to 10 weight parts, more preferably 0.01 weight parts to 5 weight parts, particularly preferably 0.05 to 1 weight parts, with respect to 100 weight parts of the water absorbent resin. When the amount of the multivalent metal compound (B) is less than 0.001 weight parts, the moisture absorption blocking property and the liquid permeability/liquid diffusing property are not sufficiently improved. When the amount of the multivalent metal compound (B) exceeds 10 weight parts, a centrifuge retention capacity (CRC), a diffusing absorbency under pressure (AAP), and the absorbency against pressure (AAP) significantly drop.

The aqueous solution of the multivalent metal compound (B) and/or the organic surface cross-linking agent (C) that can be used in the present invention are heated preferably at 30° C. or higher, more preferably at 50° C. or higher, particularly preferably at 70° C. or higher. This is based on the following reason: when a temperature of the solution is higher, it is possible to raise the concentration of the multivalent metal component contained in the solution, so that a larger amount of the multivalent metal component can exist on the surface of the water absorbent resin.

In the present embodiment, it is preferable to simultaneously mix three components: the particulate water absorbent resin (A), the organic surface cross-linking agent, and the solution of the multivalent metal compound (B).

A condition under which a precursor (D) constituted of the mixture of the particulate water absorbent resin (A), the organic surface cross-linking agent: (C), and the solution of the multivalent metal compound (B) is heated is as follows. A heating temperature is preferably 150 to 300° C., more preferably 160 to 250° C., further more preferably 170 to 230° C.

A heating time is preferably one minute to two hours, more preferably 15 minutes to 1.5 hours. A favorable example of a combination of the heating temperature and the heating time is as follows: The heating temperature is 180° C., and the heating time is 15 minutes to 1.5 hours; The heating temperature is 200° C., and the heating time is 15 minutes to one hour.

In case where the heating temperature is less than 150° C., a functional group of the organic surface cross-linking agent (C) insufficiently reacts with an acid group (for example, a carboxyl group) of the particulate water absorbent resin (A). In case where the heating temperature exceeds 300° C., the water absorbent resin is damaged while performing the heating treatment. As a result, the moisture absorption blocking property and the liquid permeation/liquid diffusing property are not sufficiently improved.

Further, in order that the water absorbent resin composition of the present embodiment has a superior moisture absorption blocking property in high humidity and a superior liquid permeation/liquid diffusing property at the same time, it is necessary that a particle surface of the water absorbent resin composition is evenly subjected to the surface treatment. The inventors first found that: in order to achieve this object, it is important that a humidification blocking ratio (wt %) of a precursor (D) is 0 wt % or more and 80 wt % or less.

In case where the humidification blocking ratio (wt %) of the precursor (D) exceeds 80 wt % and is less than 100 wt %, a large amount of coagulum are contained in the precursor (D). When the precursor (D) is heated, heat is not sufficiently conducted into the coagulum, so that the particle surfaces of the water absorbent resin composition are not secondarily cross-linked evenly. Thus, a blocking phenomenon is caused by coagulum of portions that are not secondarily cross-linked to each other. As a result, it is impossible to realize such sufficient improvement of the moisture absorption blocking property and the liquid permeation/liquid diffusing property that corresponds to an amount of the multivalent metal component added. Further, this condition may bring about such problem that: the water absorbent resin is jammed in a production apparatus due to the blocking phenomenon, so that it is impossible to stably produce the water absorbent resin composition.

A method for obtaining the precursor (D) whose humidification blocking ratio is 80 wt % or less is not particularly limited. However, it is preferable that the concentration of the multivalent metal component contained in the aqueous solution is at least 1.80 wt % in mixing the particulate water absorbent resin (A) with the multivalent metal compound (B). The solution of the highly concentrated multivalent metal compound (B) (the concentration of the multivalent metal component is at least 1.80 wt %) is mixed, so that the multivalent metal component exists around a surface layer of the water absorbent resin after mixing them. As a result, the humidification blocking property is further improved.

The concentration of the multivalent metal component contained in the solution of the multivalent metal compound (B) in obtaining the precursor (D) having a humidification blocking ratio of 80 wt % or less is preferably 1.80 wt % or more, more preferably 2.00 wt % or more, further more preferably 2.50 wt % or more, most preferably 2.90 wt % or more.

In case where the concentration of the multivalent metal component contained in the solution of the multivalent metal compound (B) is less than 1.80 wt %, the multivalent metal component permeates the water absorbent resin, so that a smaller amount of the multivalent metal component exists in a vicinity of a surface of the water absorbent resin. Thus, it is impossible to realize such sufficient improvement of the moisture absorption blocking property and the liquid permeation/liquid diffusing property that corresponds to an amount of the multivalent metal component added.

An amount of the multivalent metal compound (B) used varies depending on the desired moisture absorption blocking property and the desired liquid permeation/liquid diffusing property. However, the amount of the multivalent metal compound (B) added as the multivalent metal component is preferably 0.001 to 10 weight parts, more preferably 0.01 to 5 weight parts, particularly preferably 0.05 to 1 weight parts, with respect to 100 weight parts of solid contents. In case where the multivalent metal component is less than 0.001 weight parts, the moisture absorption blocking property and the liquid permeation/liquid diffusing property are not sufficiently improved. In case where the multivalent metal component is more than 100 weight parts, the centrifuge retention capacity (CRC), the diffusing absorbency under pressure (AAP), and the absorbency against pressure (AAP) significantly drop.

The solution of the multivalent metal compound (B) and/or the organic surface cross-linking agent (C) that can be used in the present embodiment are heated preferably at 30° C. or higher, more preferably at 50° C. or higher, particularly preferably at 70° C. or higher. This is based on the following reason: when a temperature of the solution is higher, it is possible to raise the concentration of the multivalent metal component contained in the solution, so that a larger amount of the multivalent metal component can exist on the surface of the water absorbent resin. Further, it is preferable that the upper limit temperature is less than 100° C.

In the present embodiment, it is preferable to simultaneously mix three components: the particulate water absorbent resin (A), the organic surface cross-linking agent, and the solution of the multivalent metal compound (B).

A condition under which the precursor (D) whose humidification blocking ratio is 80 wt % or less is heated is as follows. A heating temperature is preferably 150 to 300° C., more preferably 160 to 250° C., further more preferably 170 to 230° C. A heating time is preferably one minute to two hours, more preferably 15 minutes to 1.5 hours. A favorable example of a combination of the heating temperature and the heating time is as follows: The heating temperature is 180° C., and the heating time is 15 minutes to 1.5 hours; The heating temperature is 200° C., and the heating time is 15 minutes to one hour.

In case where the heating temperature is less than 150° C., a functional group of the organic surface cross-linking agent insufficiently reacts with a carboxyl group of the particulate water absorbent resin (A). In case where the heating temperature exceeds 300° C., the water absorbent resin is damaged while performing the heating treatment. As a result, the moisture absorption blocking property and the liquid permeation/liquid diffusing property are not sufficiently improved.

As to the water absorbent resin composition of the present embodiment, it is important that: specific amounts of the organic surface cross-linking agent and the multivalent metal compound (B) are added, and the organic surface cross-linking agent evenly reacts with a carboxyl group of the particulate water absorbent resin (A), and the multivalent metal component exists in a vicinity of a surface of the water absorbent resin without permeating the water absorbent resin, and the humidification blocking ratio (wt %) of the precursor (D) is 0 wt % or more and 80 wt % or less.

The following Examples and Comparative Examples will further detail the present invention. However, the present invention is not limited to them. Note that, properties of the water absorbent resin and the water absorbent resin composition were measured in accordance with the following method. Further, when a specific condition is not described, this means that all the operations were performed at room temperature (23±2° C.) and at humidity of 50 RH %.

(A) Centrifuge Retention Capacity (Referred to as CRC)

The centrifuge retention capacity (CRC) represents an absorbency at which 0.90 wt % of saline is absorbed for 30 minutes without any pressure.

0.200 g of a water absorbent resin (or a water absorbent resin composition) was evenly contained in a bag (60 mm×60 mm) made of a nonwoven fabric (Heatron Paper made by Nangoku Pulp Kogyo Co., Ltd.: model type is GSP-22). Then, the bag was heat-sealed. Thereafter, the bag was soaked in an excessively large: amount (generally, about 500 m) of 0.90 wt % sodium chloride solution (physiological saline) whose temperature had been adjusted to room temperature, and was withdrawn 30 minutes later. By using a centrifugal separator (centrifugal machine made by KOKUSAN Corporation: model type is H-122), the bag was drained for three minutes at a centrifugal force (2.50 G) recited in edana ABSORBENCY II 441, 1-99, and a weight W2 (g) of the bag was measured. Further, the same operation was performed without using the water absorbent resin, and a weight W1 (g) was measured. Then, from the weights W1 and W2, a centrifuge retention capacity (CRC) (g/g) was calculated according to the following equation.

Centrifuge retention capacity (g/g)=((weight $W2$ (g)−weight $W1$ (g))/weight (g) of water absorbent resin)−1

(B) Diffusing Absorbency Under Pressure (Referred to as DAP)

By adopting a measuring device and a measuring procedure that are recited in Japanese Unexamined Patent Publication No. 57311/1996 (Tokukaihei 8-57311), the diffusion absorbency of the water absorbent resin (or the water absorbent resin composition) was calculated as follows. A weight W3 (g) of a physiological saline absorbed by the water absorbent resin composition under a pressure of 1.9 kPa (0.3 psi) for 60 minutes was measured. Then, the diffusing absorbency (g/g) in 60 minutes after the beginning of the absorption was calculated in accordance with the following equation.

Diffusing absorbency (g/g) under pressure=weight $W3$ (g)/weight (g) of water absorbent composition (C) Absorbency Against Pressure (Referred to as AAP)

The absorbency against pressure (AAP) represents an absorbency at which 0.90 wt % of saline is absorbed for 60 minutes at 4.83 kPa.

By using an apparatus shown in FIG. 1, the absorbency against pressure (AAP) was measured. On a bottom of a plastic supporting cylinder 100 having a 60 mm internal diameter, a metal gauze 101 of stainless-steel 400 mesh (mesh size of 38 μm) was fusion-bonded. Then, under a condition of a room temperature (20° C. to 25° C.) and 50% RH relative humidity, 0.900 g of a water absorbent resin composition was evenly dispersed on the mesh. Subsequently, a piston 103 and a load 104 were placed in this order on the water absorbent resin composition. External diameters of the piston 103 and the load 104 were slightly smaller than 60 mm which was the internal diameter of the supporting cylinder 100, so that there is no gap between the piston and the supporting cylinder, and upward and downward movements of the piston 103 and the load 104 would not be hampered. Note that, the piston 103 and the load 104 were so adjusted as to evenly apply a 4.83 kPa (0.7 psi) load onto the water absorbent resin composition. Then, a weight Wa (g) of this measurement set was measured.

Inside a petri dish 105 having a 150 mm diameter, a glass filter 106 (product of Sougo Rikagaku Glass Seisakusho Co., Ltd.; diameter of fine pores: 100 μm to 120 μm) having a 90 mm diameter was placed. Thereafter, a 0.90 wt % of sodium chloride solution 108 whose temperature had been adjusted to 20° C. to 25° C. was added until it reached a level of an upper surface of the glass filter 106. Then, a piece of filter paper (product of Advantec Toyo Kaisha, Ltd.; product name: JIS P3801, No. 2; thickness: 0.26 mm; diameter of retained particles: 5 μm) having a 90 mm diameter was placed thereon, so that an entire surface of the filter paper 107 was wetted. An excess of the 0.90 wt % saline 108 was removed.

The measuring apparatus set was placed on the wet filter paper 107. Then, the water absorbent resin composition was made to absorb the 0.90 wt % saline 108 for one hour under the load of 4.83 kPa (0.7 psi). At this time, the water absorbent resin composition absorbed the 0.90 wt % saline 108 so as to be a swelling gel 102. One hour (60 minutes) later, the measuring apparatus set having absorbed the 0.90 wt % saline 108 was lifted, and a weight Wb (g) thereof was measured. From the weights Wa and Wb, the absorbency against pressure AAP (g/g) was calculated according to the following equation.

Absorbency against pressure AAP=($Wb$ (g)−$Wa$ (g))/weight (0.900) g of water absorbent resin or water absorbent resin composition)

(D) Saline Flow Conductivity (Referred to as SFC)

Calculation of the saline flow conductivity was performed in accordance with a saline flow conductivity (SFC) test recited in Published Japanese Translations of International Publication of Patent Application No. 509591/1997 (Tokuhyohei 9-509591).

By using a device shown in FIG. 1, the water absorbent resin composition (0.900 g) evenly contained in a container 40 was swelled in a synthesized urine (1) under a pressure of 0.3 psi (2.07 kPa) for 60 minutes (for 120 minutes in measuring a saline flow conductivity (SFC) retention rate), and a height of a gel layer of a gel 44 was recorded. Then, 0.69 wt % sodium chloride solution 33 was made to flow from a tank 31 and to pass through the swollen gel layer at a constant hydrostatic pressure. By using a computer and a scale, an amount of liquid passing through the gel layer at intervals of 20 seconds was recorded for 10 minutes as a time function. A flow rate $F_s(t)$ of the solution passing through the swollen gel 44 (mainly between particles thereof) was determined in terms of g/s by dividing an increasing weight (g) by an increasing time (s). A time in which a constant hydrostatic pressure and a stable flow rate had been obtained was set as "$t_s$", and only data obtained between "$t_s$" and a ten-minute interval was used to calculate the flow rate, the flow rate calculated between "$t_s$" and a ten-minute interval was used to calculate a value of $F_s(t=0)$, i.e., a first flow rate of the solution passing through the gel layer. $F_s(t=0)$ was calculated by extrapolating t=0 from a result obtained by approximating a function indicative of a relationship between $F_s(t)$ and t.

Saline Flow Conductivity=$(F_s(t=0) \times Lo)/(\rho \times A \times \Delta P)$

=$(F_s(t=0) \times Lo)/139506$

Here, $F_s(t=0)$: a flow rate represented by "g/s"

Lo: a height of the gel layer that is represented by "cm"

ρ: a density (1.003 g/cm$^3$) of NaCl solution

A: an area (28.27 cm$^2$) on the upper side of the gel layer of the cell 41

ΔP: a hydrostatic pressure (4920 dyne/cm$^2$) exerted to the gel layer. Further, a unit of the saline flow conductivity (SFC) is ($10^{-7} \times$cm$^3 \times$s$\times$g$^{-1}$).

Figure 2:
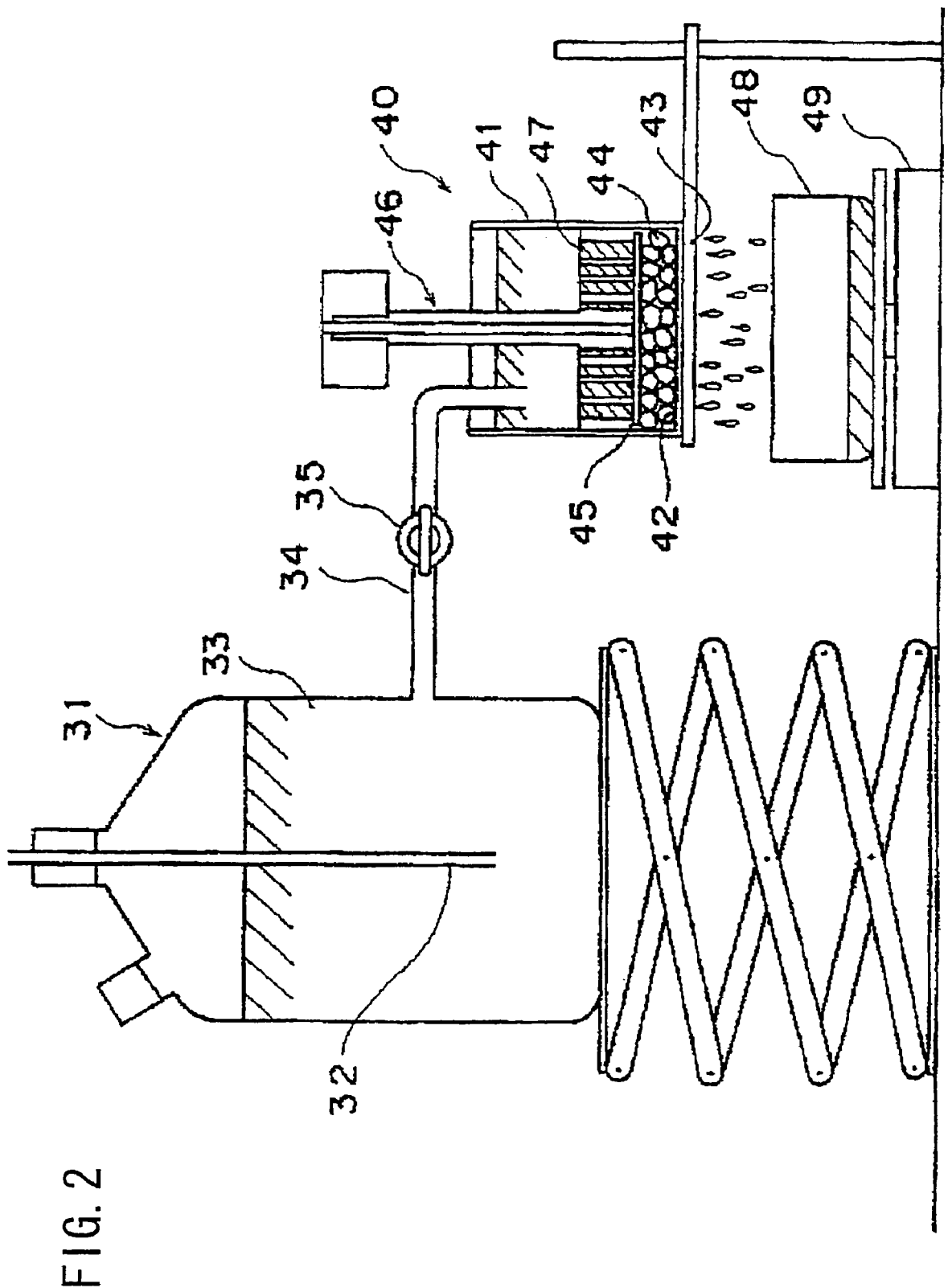
FIG. 2 is a cross sectional view schematically showing a measuring apparatus used to measure a saline flow conductivity (SFC) of the water absorbent resin composition.

In the device shown in FIG. 2, a glass tube 32 was inserted into the tank 31, and a lower end of the glass tube 32 was disposed so that 0.69 wt % sodium chloride solution 33 was positioned 5 cm higher than a bottom of the swelling gel 44 in the cell 41. 0.69 wt % sodium chloride solution 33 contained in the tank 31 was supplied to the cell 41 via an L-shaped tube 34 with a cock. A collecting container 48 for collecting liquid having passed through the gel layer was disposed under the cell 41, and the collecting container 48 was placed on an even balance 49. An inside diameter of the cell 41 was 6 cm, and No. 400 stainless metal gauze (38 µm in mesh) 42 was placed on a bottom of a lower portion of the cell 41. A hole 47 which allowed liquid to pass through was provided on a lower portion of a piston 46, and a glass filter 45 having high permeability was provided on the bottom thereof so that the water absorbent resin composition or the swelling gel did not enter into the hole 47. The cell 41 was placed on a table for the cell, and the table's surface which is in contact with the cell was positioned on the stainless metal gauze 43 which did not prevent the liquid from passing through.

The synthesized urine (1) was prepared by mixing 0.25 g of calcium chloride dihydrate, 2.0 g of potassium chloride, 0.50 g of magnesium chloride hexahydrate, 2.0 g of sodium sulfate, 0.85 g of ammonium dihydrogen phosphate, 0.15 g of ammonium dihydrogen phosphate, and 994.25 g of pure water.

(E) Moisture Absorption Blocking Ratio (wt %: Referred to as B.R.)

2 g of a water absorbent resin (or a water absorbent resin composition) was evenly sprayed on a bottom of a predetermined cup whose inside diameter was 50 mm and height was 10 mm, and was quickly placed in a constant-temperature-and-moisture apparatus (PLATINOUS LUCIFFER PL-2 G, product of TABAI ESPEC CORPORATION) in which temperature had been adjusted to 25° C. and relative humidity had been adjusted to 90%. Then, the water absorbent resin or the water absorbent resin composition was left in the constant-temperature-and-moisture apparatus for 60 minutes. Thereafter, the water absorbent resin that had absorbed moisture was moved onto a JIS standard sieve (diameter is 7.5 cm, mesh size is 2000 µm), and was sieved for a certain time by using a sieve shaker (IIDA SIEVE SHAKER, TYPE: ES-65, SER. No. 0501). Then, a weight W4 (g) of the water absorbent resin which remained on the sieve and a weight W5 (g) of the water absorbent resin which passed through the sieve were measured. Note that, it took less than 10 minutes to finish measuring the weights W4 (g) and W5 (g) after having picked up the water absorbent resin from the constant-temperature-and-moisture apparatus.

Then, the moisture absorption blocking ratio (wt %) was calculated in accordance with the following equation. As the moisture absorption blocking ratio is lower, the water absorbent resin is superior in terms of the moisture absorption blocking property.

Moisture absorption blocking ratio (wt %)=weight W4 (g)/(weight W4 (g)+weight W5 (g))×100

Note that, in the present embodiment, the moisture absorption blocking ratio (wt %) was calculated by setting the predetermined cup and the sieving time of the sieve shaker under the following two conditions.

(a) An aluminum cup (Foil Container, Product No. 107, Product of TOYO ECKO Inc.) whose bottom diameter was 52 mm and height was 22 mm was used as the predetermined cup and the water absorbent resin was sieved for 8 seconds by the sieve shaker so as to measure a moisture absorption blocking ratio (wt %). Hereinafter, the moisture absorption blocking ratio calculated under this condition is referred to as a moisture absorption blocking ratio a (B. R. a).

(b) A polypropylene cup whose bottom diameter was 50 mm and height was 10 mm was used as the predetermined cup and the water absorbent resin was sieved for five minutes by the sieve shaker so as to measure a moisture absorption blocking ratio (wt %). Hereinafter, the moisture absorption blocking ratio calculated under this condition is referred to as a moisture absorption blocking ratio b (B.R.b).

(F) Weight Average Particle Diameter (D50) and Logarithmic Standard Deviation (σζ) of Particle Size Distribution The water absorbent resin or the water absorbent was sieved by using JIS standard sieves respectively having mesh sizes of 850 µm, 710 µm, 600 µm, 500 µm, 425 µm, 300 µm, 212 µm, 150 µm, 45 µm, and the like, and a residual percentage R was plotted on a logarithmic probability paper. Then, a particle diameter corresponding to R=50 wt % was read as the weight average particle diameter (D50). Further, assuming that X1 is a particle diameter in case where R=84.1% and X2 is a particle diameter in case where R=15.9, the logarithmic standard deviation (σζ) is represented by the following equation. As a value of σζ is smaller, the particle size distribution is narrower.

$$\sigma\zeta = 0.5 \times \ln(X2/X1)$$

Classification in measuring the logarithmic standard deviation (σζ) of the particle size distribution was performed as follows: 10.0 g of the water absorbent resin particles or the water absorbent was spread on JIS standard sieves (THE IIDA TESTING SIEVE: diameter is 8 cm) respectively having mesh sizes of 850 µm, 710 µm, 600 µm, 500 µm, 425 µm, 300 µm, 212 µm, 150 µm, and 106 µm, and was classified by using a sieve shaker (IIDA SIEVE SHAKER, TYPE: ES-65, SER. No. 0501) for five minutes.

(G) Multivalent Metal Component Extraction Rate (wt %)

An amount of the multivalent metal component contained in the water absorbent resin was determined as follows.

1.0 g of the water absorbent resin composition was measured and placed in a polypropylene beaker of 260 ml, and 190.0 g of physiological saline (0.9 wt % NaCl aqueous solution) and 10.0 g of 2N hydrochloric acid were added thereto, and thus obtained mixture was stirred for 30 minutes at room temperature. After stirring them, supernatant liquid thereof was filtered by using a chromatodisc (GL Chromatodisc 25A, product of GL Science Inc.), and was analyzed by plasma emission spectrochemical analysis (by using ULTIMA, product of HORIBA, Ltd.), thereby calculating the multivalent metal component concentration. Note that, an analytical curve was made in accordance with physiological saline containing a known amount of the multivalent metal component. On the basis of the calculated multivalent metal component concentration, the multivalent metal component concentration in the water absorbent resin composition is represented by the following equation.

Multivalent metal component concentration (wt %) in the water absorbent resin composition=(multivalent metal component concentration (wt %) in solution)×200

The multivalent metal component extraction rate was measured as follows.

Solution A was prepared by mixing 95 g of methanol solution of 1.0 wt % 8-quinolinol (product of Wako Pure Chemical Industries, Ltd.) with 5 g of pure water, and solution B was prepared by mixing 95 g of methanol with 5 g of pure water.

A teflon (registered trademark) rotor whose diameter was 35 mm was placed in a 260 ml polypropylene container, and 5 g of the water absorbent resin composition and 25 g of the solution A were measured and poured therein. The container was tightly closed, and the content was stirred by using a magnetic stirrer for 20 hours at room temperature. 5 ml of supernatant liquid thereof was picked up by using a polypropylene syringe, and a chromatodisc (GL chromatodisc 25A, product of GL Science Inc.) was provided on the syringe, and the filtered liquid was placed in a polypropylene container. Part of the filtered liquid was moved to a 1 cm cell (disposable cuvet purchased from AS ONE CORPORATION.: product number is 2-478-03, model number is 1939) made of plastic, and a light absorbance at which a complex constituted of the multivalent metal component and 8-quinolinol absorbs light of specific wavelength was measured by using a spectrophotometer (Hitachi spectrophotometer U-1100). For example, when the multivalent metal component is aluminum, the specific wavelength was 380 nm. Hereinafter, for the convenience in description, the specific wavelength is explained on the assumption that the multivalent metal component is aluminum. When the light absorbance at which the filtered liquid absorbed light having 280 nm wavelength exceeded a measurement limit of the spectrophotometer, the filtered liquid was diluted by the solution B so that the light absorbance was within a measurable range of the spectrophotometer. Then, the measurement was performed.

Further, as the light absorbance at the time of extraction of 100 wt % multivalent metal component, measurement was performed with respect also to a light absorbance at which light of 380 nm wavelength was absorbed by a solution obtained by dissolving the multivalent metal component in the solution A so that there is the same amount of the multivalent metal component as at the time of extraction of 100 wt % multivalent metal component (the concentration of the multivalent metal component in the water absorbent resin composition was separately measured in the foregoing manner).

The extraction rate of the multivalent metal component was calculated in accordance with the following equation.

Extraction rate ($wt$ %) of the multivalent metal component=((filtered liquid's light absorbance with respect to light of 380 nm wavelength)−(solution A's light absorbance with respect to light of 380 nm wavelength))/(light absorbance with respect to light of 380 nm wavelength at the time of extraction of 100 $wt$ % multivalent metal component)×100

(H) Humidification Blocking Ratio (wt %)

In the present embodiment, the humidification blocking ratio calculated by the following measurement method is regarded as an index of a humidification blocking property of the precursor (D).

In five minutes after the beginning of the mixture, 10 g of the precursor (D) constituted of the mixture of the particulate water absorbent resin (A), aqueous solution of the multivalent metal compound (B), and/or the organic surface cross-linking agent (C) was moved onto a JIS standard sieve (diameter is 7.5 cm, mesh size is 1000 μm), and was sieved by using a sieve shaker (IIDA SIEVE SHAKER, TYPE: ES-65, SER. No. 0501) for 10 seconds, and a weight W6 (g) of the water absorbent resin remaining on the sieve and a weight W7 (g) of the water absorbent resin passing through the sieve were measured. The humidification blocking ratio (wt %) was calculated in accordance with the following equation. As the humidification blocking ratio is lower, the precursor (D) is superior in terms of the humidification blocking property.

Humidification blocking ratio ($wt$ %)=weight $W6$ (g)/(weight $W6$ (g)+weight $W7$ (g))×100

(I) Amount of Water-Soluble Component (Soluble Component)

184.3 g of a 0.9 wt % saline was measured and poured into a 250 ml plastic container having a cover. Into the saline, 1.00 g of a water absorbent resin composition was added, and the saline was stirred for 16 hours by rotating a stirrer, thereby preparing a water-soluble component extract solution in which soluble component of the water absorbent resin composition was extracted. The water-soluble component extract solution was filtered through a piece of filter paper (product of Advantec Toyo Kaisha, Ltd.; product name: JIS P3801, No. 2; thickness: 0.26 mm; diameter of retained particles: 5 μm), thereby obtaining a filtrate. 50.0 g of the filtrate was measured, and used as a measurement solution. The following description explains a method for measuring the amount of the soluble component of the water absorbent resin composition by using the measurement solution.

First, 0.9 wt % of the saline to which the water absorbent resin composition had not been added was titrated by using a 0.1N NaOH solution, until pH of the saline reached 10. In this way, a titration amount ([bNaOH]ml) of 0.1N NaOH solution which was required so that pH of the saline reached 10 was measured. After that, the 0.1N HCl solution was titrated until pH of the saline reached 2.7. In this way, a titration amount ([bHCl]ml) of 0.1N HCl solution which was required so that pH of the saline reached 2.7 was measured.

The same titration was performed with respect to the measurement solution. As a result, a titration amount ([NaOH]ml) of 0.1N NaOH solution which was required so that pH of the measurement solution reached 10 was measured, and a titration amount ([HCl]ml) of 0.1N HCl solution which was required so that pH of the measurement solution reached 2.7 was obtained.

For example, in case where a water absorbent resin composition includes a known amount of acrylic acid and its sodium chloride, it is possible to calculate an amount of soluble component in the water absorbent resin composition, in accordance with the following, from an average molecular mass of the monomer and the titration amounts ([bNaOH]ml, [bHCl]ml, [NaOH]ml, and [HCl]ml) obtained by the foregoing operation.

Amount of soluble component (weight %)=0.1×(average molecular mass)×184.3×100×([HCl]ml−[NaOH]ml)/1000/1.0/50.0

Further, it is possible to calculate a neutralization rate of the water absorbent resin composition in accordance with the following equation.

Neutralization ratio ($mol$ %)=(1−([NaOH]ml−[$b$NaOH]ml)/([HCl]ml−[$b$HCl]ml))×100

In case of using a water absorbent rein composition constituted of a component whose amount was unknown, it is possible to calculate the average molecular mass of the monomer by using the foregoing neutralization rate.

(J) Absorption Rate (Vortex)

A blue-colored physiological saline whose temperature had been adjusted to 30° C. and a white stirrer (Teflon (trade name), mentioned in Union Catalogue Version 2,000 published by FLON INDUSTRY CO., LTD., Teflon (trade name) stirrer SA type, product No. SA-40, total length 40 mm×diameter 8 mm) were placed in a beaker of 100 ml (TOP beaker CAT. No. 501, based on JIS R-3503, which is mentioned in GENERAL CATALOGUE A-7000 published by Sogo Rikagaku Glass Industry Co., Ltd.: periphery×height=55 (mm)×70 (mm)) in advance, and the physiological saline was stirred by a magnetic stirring device at a speed of 600 rpm. When 2.0 g of the water absorbent resin composition was added to the physiological saline, gelation of the test solution was proceeded, and a swirl was diminished, so that the test solution surrounded the stirrer.

Then, a time (second) since the water-absorbent resin had been added to the test solution until the stirrer was surrounded by the test solution was measured, and the time (second) was regarded as the absorption rate. Note that, in the present embodiment, the time until the stirrer was surrounded by the test solution was a period until the rotating stirrer that had been seen was hidden by the protuberant swirl that had almost disappeared.

The blue physiological saline is composed of: 991 mass parts of deionized water, 9 mass parts of sodium chloride, and 0.02 mass parts of food additive•edible Brilliant Blue. (food additive•edible brilliant blue: benzyl-ethyl-[4'-(4"-benzyl ethyl amino)-diphenyl methylene)-2',5-cyclohexa dienylidene]-ammonium-2''',3,3'''-disodium trisulfonic acid; brilliant blue FCF; CI No. 42090; CI Food blue 2)

Referential Example 1

4.0 g of polyethyleneglycoldiacrylate (average added mole number of ethylene oxide: 8) were dissolved in a 5500 g of a sodium acrylate solution (monomer concentration: 38 mass %) having a 75 mol % neutralization ratio, so as to prepare a reaction solution. Then, the reaction solution was deaerated for 30 minutes in an atmosphere of nitrogen gas, and was fed to a reactor that had been prepared by placing a lid on a 10 L stainless-steel double-arm kneader equipped with two sigma blades and a jacket. Inside the reactor was replaced with nitrogen gas while maintaining the temperature of the reaction solution at 30° C. Subsequently, 2.8 g of sodium persulfate and 0.01 g of L-ascorbic acid were added to the reaction solution, while the reaction solution was stirred. Approximately one minute later, polymerization was initiated. During the polymerization, the reaction solution was kept at 30° C. to 90° C. In 60 minutes after the polymerization was initiated, a water-containing gelled polymer was retrieved. Thus obtained water-containing gelled polymer had been fragmented so that its diameter was approximately 5 mm. The water-containing gelled polymer fragmented was spread out on a wire mesh of 50 mesh (mesh size is 300 μm), and was dried by hot air at 150° C. for 90 minutes. A dry polymer thus obtained was crushed by using a vibrating mill, and then classified by using a wire mesh of 20 meshes (mesh size is 850 μm) then blended. Thus, water absorbent resin powder (a) having a crushed indeterminate form was obtained. In 100 parts of thus obtained water absorbent resin powder (a), a surface cross-linking solvent including 0.5 weight parts of propyleneglycol, 0.03 weight parts of ethyleneglycol diglycidyl ether, 0.3 weight parts of 1,4-butanediol, and three weight parts of water, was mixed. The mixture was then thermally processed at 200° C. for 5.5 minutes, thereby obtaining a water absorbent resin (1). Table 1 shows a particle size distribution of the water absorbent resin (1), and Table 2 shows other properties of the water absorbent resin (1).

Referential Example 2

4.0 g of polyethyleneglycoldiacrylate (average added mole number of ethylene oxide: 8) were dissolved in a 5500 g of a sodium acrylate solution (monomer concentration: 38 mass %) having a 75 mol % neutralization ratio, so as to prepare a reaction solution. Then, the reaction solution was deaerated for 30 minutes in an atmosphere of nitrogen gas, and was fed to a reactor that had been prepared by placing a lid on a 10 L stainless-steel double-arm kneader equipped with two sigma blades and a jacket. Inside the reactor was replaced with nitrogen gas while maintaining the temperature of the reaction solution at 30° C. Subsequently, 2.8 g of sodium persulfate and 0.01 g of L-ascorbic acid were added to the reaction solution, while the reaction solution was stirred. Approximately one minute later, polymerization was initiated. During the polymerization, the reaction solution was kept at 30° C. to 90° C. In 60 minutes after the polymerization was initiated, a water-containing gelled polymer was retrieved. Thus obtained water-containing gelled polymer had been fragmented so that its diameter was approximately 5 mm. The water-containing gelled polymer fragmented was spread out on a wire mesh of 50 mesh (mesh size is 300 μm), and was dried by hot air at 150° C. for 90 minutes. A dry polymer thus obtained was crushed by using a vibrating mill, and then classified by using a wire mesh of 20 meshes (mesh size is 850 μm) then blended. Thus, water absorbent resin powder (b) having a crushed indeterminate form was obtained. In 100 parts of thus obtained water absorbent resin powder (b), a surface cross-linking solvent including 0.5 weight parts of propyleneglycol, 0.03 weight parts of ethyleneglycol diglycidyl ether, 0.3 weight parts of 1,4-butanediol, and three weight parts of water, was mixed. The mixture was then thermally processed at 200° C. for 55 minutes, thereby obtaining a water absorbent resin (2). Table 1 shows a particle size distribution of the water absorbent resin (2), and Table 2 shows other properties of the water absorbent resin (2).

Referential Example 3

Unlike the Referential Example 1, the dry polymer was crushed by using a pin mill instead of the vibrating mill, and then classified by using a wire mesh of 20 meshes (mesh size is 850 μm) then blended. Thus, water absorbent resin powder (C) having a crushed indeterminate form was obtained. Thus obtained water absorbent resin powder (C) was subjected to the same treatment as in the Referential Example 1, thereby obtaining a water absorbent resin (3). Table 1 shows a particle size distribution of the water absorbent resin (3), and Table 2 shows other properties of the water absorbent resin (3).

Referential Example 4

In the present Referential Example, 11.8 g of polyethyleneglycoldiacrylate (average added mole number of ethylene oxide: 8) were dissolved in a 5500 g of a sodium acrylate solution (monomer concentration: 38 mass %) having a 75 mol % neutralization ratio, so as to prepare a reaction solution. Then, the reaction solution was deaerated for 30 minutes in an atmosphere of nitrogen gas, and was fed to a reactor that had been prepared by placing a lid on a 10 L stainless-steel double-arm kneader equipped with two sigma blades and a jacket. Inside the reactor was replaced with nitrogen gas while maintaining the temperature of the reaction solution at 30° C. Subsequently, 2.8 g of sodium persulfate and 0.01 g of L-ascorbic acid were added to the reaction solution, while the reaction solution was stirred. Approximately one minute later, polymerization was initiated. During the polymerization, the reaction solution was kept at 30° C. to 90° C. In 60 minutes after the polymerization was initiated, a water-containing gelled polymer was retrieved. Thus obtained water-containing gelled polymer had been fragmented so that its diameter was approximately 5 mm. The water-containing gelled polymer fragmented was spread out on a wire mesh of 50 mesh (mesh size is 300 μm), and was dried by hot air at 150° C. for 90 minutes. A dry polymer thus obtained was crushed by using a vibrating mill, and then classified by using a wire mesh of 30 meshes (mesh size is 600 μm) then blended. Thus, water absorbent resin powder (D) having a crushed indeterminate form was obtained. In 100 parts of thus obtained water absorbent resin powder (D), a surface cross-linking solvent including 0.5 weight parts of propyleneglycol, 0.03 weight parts of ethyleneglycol diglycidyl ether, 0.3 weight parts of 1,4-butanediol, and three weight parts of water, was mixed. The mixture was then thermally processed at 200° C. for 55 minutes, thereby obtaining a water absorbent resin (4). Table 1 shows a particle size distribution of the water absorbent resin (4), and Table 2 shows other properties of the water absorbent resin (4).

Referential Example 5

Unlike the Referential Example 1, the dry polymer was crushed by using a roll mill instead of the vibrating mill, and then classified by using a wire mesh of 20 meshes (mesh size is 850 μm) then blended. Thus, water absorbent resin powder (E) having a crushed indeterminate form was obtained. Thus obtained water absorbent resin powder (E) was subjected to the same treatment as in the Referential Example 1, thereby obtaining a water absorbent resin (5). Table 1 shows a particle size distribution of the water absorbent resin (5), and Table 2 shows other properties of the water absorbent resin (5).

Example 1

5.4 weight parts of 51.2 mass % aluminum sulfate hydrate (tetradecahydrate to octadecahydrate) was added and mixed with 100 weight parts of the water absorbent resin (1) obtained in the Referential Example 1, thereby obtaining a water absorbent resin composition (1). Table 1 shows a particle size distribution of the water absorbent resin composition (1), and Table 2 shows other properties of the water absorbent resin composition (1).

Example 2

6.7 weight parts of 40.9 mass % aluminum sulfate hydrate (tetradecahydrate to octadecahydrate) was added and mixed with 100 weight parts of the water absorbent resin (1) obtained in the Referential Example 1, thereby obtaining a water absorbent resin composition (2). Table 1 shows a particle size distribution of the water absorbent resin composition (2), and Table 2 shows other properties of the water absorbent resin composition (2).

Example 3

9.0 weight parts of 30.8 mass % aluminum sulfate hydrate (tetradecahydrate to octadecahydrate) was added and mixed with 100 weight parts of the water absorbent resin (1) obtained in the Referential Example 1, thereby obtaining a water absorbent resin composition (3). Table 1 shows a particle size distribution of the water absorbent resin composition (3), and Table 2 shows other properties of the water absorbent resin composition (3).

Example 4

5.4 weight parts of 51.2 mass % aluminum sulfate (tetradecahydrate to octadecahydrate) hydrate was added and mixed with 100 weight parts of the water absorbent resin (4), obtained in the Referential Example 4, whose powder temperature was 60° C., thereby obtaining a water absorbent resin composition (8). Table 1 shows a particle size distribution of the water absorbent resin composition (8), and Table 2 shows other properties of the water absorbent resin composition (8).

Comparative Example 1

18.0 weight parts of 15.3 mass % aluminum sulfate hydrate (tetradecahydrate to octadecahydrate) was added and mixed with 100 weight parts of the water absorbent resin (1) obtained in the Referential Example 1, thereby obtaining a water absorbent resin composition (4). Table 1 shows a particle size distribution of the water absorbent resin composition (4), and Table 2 shows other properties of the water absorbent resin composition (4).

Comparative Example 2

2 weight parts of aluminum sulfate hydrate (tetradecahydrate to octadecahydrate) in a powder form was added and mixed with 100 weight parts of the water absorbent resin (1) obtained in the Referential Example 1, thereby obtaining a water absorbent resin composition (5). Table 1 shows a particle size distribution of the water absorbent resin composition (5), and Table 2 shows other properties of the water absorbent resin composition (5).

Comparative Example 3

A surface cross-linking solvent constituted of 0.5 weight parts of propyleneclycol, 0.03 weight parts of ethyleneglycol diglycidyl ether, 0.3 weight parts of 1,4-butanediol, and three weight parts of water was mixed with 100 weight parts of the water absorbent resin powder (a) of the Referential Example 1, and 9.0 weight parts of 30.8 mass % aluminum sulfate (tetradecahydrate to octadecahydrate) hydrate was added and mixed therewith. Then, thus obtained mixture was thermally processed at 200° C. for 55 minutes, thereby obtaining a water absorbent resin (6). Table 1 shows a particle size distribution of the water absorbent resin composition (6), and Table 2 shows other properties of the water absorbent resin composition (6).

Comparative Example 4

6.7 weight parts of 40.9 mass % aluminum sulfate hydrate (tetradecahydrate to octadecahydrate) was added and mixed with 100 weight parts of the water absorbent resin (1) obtained in the Referential Example 2, thereby obtaining a water absorbent resin composition (7). Table 1 shows a particle size distribution of the water absorbent resin composition (7), and Table 2 shows other properties of the water absorbent resin composition (7).

Comparative Example 5

5.4 weight parts of 51.2 mass % aluminum sulfate hydrate (tetradecahydrate to octadecahydrate) was added and mixed with 100 weight parts of the water absorbent resin (3) obtained in the Referential Example 3, thereby obtaining a water absorbent resin composition (7). Table 1 shows a particle size distribution of the water absorbent resin composition (7), and Table 2 shows other properties of the water absorbent resin composition (7).

Comparative Example 6

6.7 weight parts of 40.9 mass % aluminum sulfate hydrate (tetradecahydrate to octadecahydrate) was added and mixed with 100 weight parts of the water absorbent resin (5) obtained in the Referential Example 5, thereby obtaining a water absorbent resin composition (7). Table 1 shows a particle size distribution of the water absorbent resin composition (7), and Table 2 shows other properties of the water absorbent resin composition (7).

TABLE 1

| | Referential Example 1 | Referential Example 2 | Referential Example 3 | Referential Example 4 | Referential Example 5 |
|---|---|---|---|---|---|
| 850 µm or more | 0.0 | 0.0 | 0.0 | 0.0 | 0.5 |
| less than 850 µm, 710 µm or more | 0.9 | 0.8 | 0.0 | 0.0 | 6.6 |
| less than 710 µm, 600 µm or more | 6.5 | 5.5 | 0.1 | 0.0 | 15.0 |
| less than 600 µm, 500 µm or more | 20.9 | 19.4 | 3.6 | 2.7 | 33.3 |
| less than 500 µm, 425 µm or more | 15.2 | 16.2 | 9.2 | 19.1 | 26.2 |
| less than 425 µm, 300 µm or more | 28.5 | 26.5 | 23.3 | 36.2 | 10.5 |
| less than 300 µm, 212 µm or more | 14.9 | 12.9 | 38.2 | 26.6 | 6.3 |
| less than 212 µm, 150 µm or more | 8.1 | 8.7 | 20.8 | 12.6 | 1.5 |
| less than 150 µm, 106 µm or more | 4.0 | 8.0 | 4.0 | 2.6 | 0.1 |
| less than 106 µm, 45 µm or more | 1.0 | 2.0 | 0.8 | 0.1 | 0.0 |
| less than 45 µm | 1.0 | 2.0 | 0.0 | 0.0 | 0.0 |
| LOGARITHMIC STANDARD DEVIATION (σζ) | 0.43 | 0.51 | 0.38 | 0.36 | 0.23 |
| D50 (µm) | 394.00 | 383.00 | 266.00 | 322.00 | 514.00 |

| | Example 1 | Example 2 | Example 3 | Example 4 |
|---|---|---|---|---|
| 850 µm or more | 0.0 | 0.0 | 0.0 | 0.0 |
| less than 850 µm, 710 µm or more | 0.9 | 0.9 | 0.9 | 0.0 |
| less than 710 µm, 600 µm or more | 8.0 | 7.0 | 7.0 | 0.3 |
| less than 600 µm, 500 µm or more | 26.8 | 25.9 | 26.0 | 3.0 |
| less than 500 µm, 425 µm or more | 19.3 | 19.2 | 18.7 | 20.3 |
| less than 425 µm, 300 µm or more | 26.6 | 26.5 | 26.0 | 35.7 |
| less than 300 µm, 212 µm or more | 12.7 | 12.6 | 13.0 | 26.9 |
| less than 212 µm, 150 µm or more | 5.0 | 5.8 | 5.8 | 11.8 |
| less than 150 µm, 106 µm or more | 0.5 | 1.7 | 2.0 | 1.9 |
| less than 106 µm, 45 µm or more | 0.2 | 0.4 | 0.6 | 0.1 |
| less than 45 µm | 0.2 | 0.4 | 0.6 | 0.0 |
| LOGARITHMIC STANDARD DEVIATION (σζ) | 0.34 | 0.36 | 0.37 | 0.35 |
| D50 (µm) | 443 | 436 | 434 | 327 |

| | Comparative Example 1 | Comparative Example 2 | Comparative Example 3 | Comparative Example 4 | Comparative Example 5 | Comparative Example 6 |
|---|---|---|---|---|---|---|
| 850 µm or more | 0.0 | 0.0 | 0.0 | 0.0 | 0.0 | 1.2 |
| less than 850 µm, 710 µm or more | 1.2 | 1.1 | 1.1 | 1.1 | 0.0 | 8.9 |
| less than 710 µm, 600 µm or more | 11.3 | 7.2 | 10.8 | 7.5 | 0.5 | 19.9 |
| less than 600 µm, 500 µm or more | 23.6 | 21.0 | 24.4 | 22.1 | 4.8 | 31.8 |
| less than 500 µm, 425 µm or more | 17.1 | 15.4 | 16.3 | 19.8 | 13.9 | 24.2 |
| less than 425 µm, 300 µm or more | 26.8 | 28.2 | 26.6 | 23.4 | 26.1 | 8.1 |
| less than 300 µm, 212 µm or more | 14.3 | 14.3 | 14.1 | 10.9 | 33.5 | 5.0 |
| less than 212 µm, 150 µm or more | 2.4 | 7.9 | 2.9 | 7.5 | 17.1 | 0.8 |
| less than 150 µm, 106 µm or more | 2.8 | 4.0 | 2.8 | 6.5 | 3.8 | 0.1 |

TABLE 1-continued

| | | | | | | |
|---|---|---|---|---|---|---|
| less than 106 μm, 45 μm or more | 0.5 | 0.9 | 1.0 | 1.2 | 0.3 | 0.0 |
| less than 45 μm | 0.5 | 0.9 | 1.0 | 1.2 | 0.0 | 0.0 |
| LOGARITHMIC STANDARD DEVIATION (σζ) | 0.37 | 0.43 | 0.37 | 0.47 | 0.4 | 0.21 |
| D50 (μm) | 437 | 399 | 436 | 427 | 287 | 534 |

TABLE 2

| | A | B | C | D | E | F | G | H | I | J | K | L |
|---|---|---|---|---|---|---|---|---|---|---|---|---|
| Referential Example 1 | — | — | — | 34.0 | 32.0 | 100 | — | 23.3 | 71.0 | | 0.43 | 394.0 |
| Referential Example 2 | — | — | — | 34.2 | 32.3 | 100 | — | 23 | 69 | | 0.51 | 383 |
| Referential Example 3 | — | — | — | 34.4 | 32.3 | 100 | — | 22.1 | 45.0 | | 0.38 | 266.0 |
| Referential Example 4 | — | — | — | 27.5 | 24.3 | 90 | — | 8.6 | 60.0 | 75.0 | 0.36 | 322.0 |
| Referential Example 5 | — | — | — | 34.4 | 32.1 | 100 | — | 24.3 | 121 | | 0.23 | 514 |
| Example 1 | 51.2 | 1.0 | 0.24 | 32.8 | 30.3 | 0 | 14.6 | 24.2 | 57 | | 0.34 | 443 |
| Example 2 | 40.9 | 0.8 | 0.24 | 32.2 | 28.8 | 0 | 10.5 | 24.9 | 53 | | 0.36 | 436 |
| Example 3 | 30.8 | 0.6 | 0.24 | 31.3 | 28.1 | 0 | 7.6 | 22 | 51 | | 0.37 | 434 |
| Example 4 | 51.2 | 1 | 0.24 | 27.3 | 24.0 | 0 | 14.8 | 8.2 | 40 | 120.0 | 0.35 | 327 |
| Comparative Example 1 | 15.3 | 0.3 | 0.24 | 28.2 | 27.0 | 35 | 4.6 | 23.2 | 53 | | 0.37 | 437 |
| Comparative Example 2 | — | — | 0.17 | 33.2 | 28.1 | 90 | 100 | 24.5 | 56 | | 0.43 | 399 |
| Comparative Example 3 | 30.8 | 0.6 | 0.24 | 30.2 | 25.9 | 50 | 4.3 | 21.3 | | | 0.37 | 436.0 |
| Comparative Example 4 | 40.9 | 0.8 | 0.24 | 32.5 | 28.0 | 100 | 3.4 | 24.1 | 53 | | 0.47 | 427 |
| Comparative Example 5 | 30.8 | 0.6 | 0.24 | 30.2 | 25.9 | 50 | 4.3 | 23.0 | 31.0 | | 0.4 | 287.0 |
| Comparative Example 6 | 40.9 | 0.8 | 0.24 | 32.5 | 28.0 | 100 | 3.4 | 24.8 | 101 | | 0.21 | 534 |

Signs in this table are as follows:
A: Concentration (mass %) of the aqueous solution of the aluminum sulfate hydrate (tetradecahydrate to octadecahydrate)
B: Ratio of concentration of the solution of the multivalent metal compound (Solution concentration of the multivalent metal compound used/Unsaturated solution concentration of the multivalent metal compound)
C: Amount (mass %) of the multivalent metal component added
D: Absorbency (g/g)
E: Diffusing absorbency under pressure (g/g)
F: Moisture absorption blocking ratio (%)
G: Extraction rate (mass %) of the multivalent metal
H: Water-soluble component amount (wt %)
I: Absorption rate (second)
J: Saline flow conductivity ($10^{-7} \times cm^3 \times s \times g^{-1}$)
K: Logarithmic standard deviation (σζ)
L: Weight average particle diameter (μm)

Referential Example 6

In a reactor that had been prepared by placing a lid on a 10 L stainless-steel double-arm kneader equipped with two sigma blades and a jacket, 11.7 g (0.10 mol %) of polyethyleneglycoldiacrylate was dissolved in 5438 g (monomer concentration of 39 wt %) of sodium acrylate aqueous solution having a neutralization rate of 71.3 mol %, thereby preparing a reaction solution. Next, the reaction solution was deaerated for 30 minutes in an atmosphere of nitrogen gas. Subsequently, 29.34 g of 10 wt % potassium persulfate aqueous solution and 24.25 g of 1 wt % L-ascorbic acid were added to the reaction solution, while the reaction solution was stirred. Approximately one minute later, polymerization was initiated. While crushing the generated gel, the polymerization was performed at 20° C. to 95° C. In 30 minutes after the polymerization was initiated, a water-containing gel cross-linking polymer was retrieved. Thus obtained water-containing gel cross-linking polymer had been fragmented so that its diameter was approximately 5 mm. The water-containing gel cross-linking polymer fragmented was spread out on a wire mesh of 50 mesh (mesh size is 300 μm), and was dried by hot air at 175° C. for 50 minutes, thereby obtaining a water absorbent resin (A), constituted of particulate or powdery dried substances, which had an indeterminate form and was easily crushed.

Thus obtained water absorbent resin (A) was crushed by using a roll mill, and then classified by using a JIS standard sieve (mesh size is 850 μm). Next, particles having passed through the mesh of 850 μm were classified by using a JIS standard sieve (mesh size is 150 μm), so that the water absorbent resin passing through the mesh of 150 μm were removed, thereby obtaining a particulate water absorbent resin (A1).

Further, the water absorbent resin (A) obtained in the same manner was crushed by using a roll mill, and then classified by using a JIS standard sieve (mesh size is 710 μm). Next, particles having passed through the mesh of 710 μm were classified by using a JIS standard sieve (mesh size is 150 μm), so that the water absorbent resin passing through the mesh of 150 μm were removed, thereby obtaining a particulate water absorbent resin (A2).

Further, the water absorbent resin (A) obtained in the same manner was crushed by using a roll mill, and then classified by using a JIS standard sieve (mesh size is 600 μm). Next, particles having passed through the mesh of 600 μm were classified by using a JIS standard sieve (mesh size is 150 μm), so that the water absorbent resin passing through the mesh of 150 μm were removed, thereby obtaining a particulate water absorbent resin (A3).

Further, the water absorbent resin (A) obtained in the same manner was crushed by using a roll mill, and then classified by using a JIS standard sieve (mesh size is 710 μm). Next, particles having passed through the mesh of 710 μm were classified by using a JIS standard sieve (mesh size is 106 μm), so that the water absorbent resin passing through the mesh of 106 μm were removed, thereby obtaining a particulate water absorbent resin (A4).

Example 5

A surface treatment agent constituted of a mixture solution obtained by mixing 0.3 g of 1,4-butanediol, 0.3 g of propyleneglycol, 1.5 g of pure water, and 1.0 g of aluminum sulfate detradecahydrate was evenly mixed with 100 g of the water absorbent resin (A1) obtained in the Referential Example 6, thereby obtaining a precursor (1). Thus obtained precursor (1) was thermally processed at 180° C. for 30 minutes. Further, particles thereof were fragmented so as to pass through a JIS standard sieve (mesh size is 850 μm), thereby obtaining a water absorbent resin composition (1). Table 4 shows a result obtained by measuring properties of the water absorbent resin composition (1).

Example 6

A surface treatment agent constituted of a mixture solution obtained by mixing 1.0 g of ethyleneglycol, 2.0 g of pure water, and 0.8 g of aluminum chloride 6 hydrate was evenly mixed with 100 g of the water absorbent resin (A1) obtained in the Referential Example 6. Thereafter, thus obtained mixture was thermally processed at 200° C. for 25 minutes. Further, particles thereof were fragmented so as to pass through a JIS standard sieve (mesh size is 850 μm), thereby obtaining a water absorbent resin composition (2). Table 4 shows a result obtained by measuring properties of the water absorbent resin composition (2).

Comparative Example 7

A surface treatment agent constituted of a mixture solution obtained by mixing 0.3 g of 1,4-butanediol, 0.3 g of propyleneglycol, 4 g of pure water, and 1.0 g of aluminum sulfate tetradecahydrate was evenly mixed with 100 g of the water absorbent resin (A1) obtained in the Referential Example 6. Thereafter, thus obtained mixture was heated at 180° C. for 30 minutes. Further, particles thereof were fragmented so as to pass through a JIS standard sieve (mesh size is 850 μm), thereby obtaining a comparative water absorbent resin composition (1). Table 4 shows a result obtained by measuring properties of the comparative water absorbent resin composition (1).

Comparative Example 8

With reference to Example recited in Published Japanese Translations of International Publication of Patent Application No. 539281/2002 (Tokuhyo 2002-539281) (WO00/53644), the following experiment was performed.

A surface treatment agent constituted of a mixture solution obtained by mixing 1.0 g of ethyleneglycol, 3.0 g of pure water, and 0.5 g of aluminum sulfate tetradecahydrate was evenly mixed with 100 g of the water absorbent resin (A1) obtained in the Referential Example 6, thereby obtaining a comparative precursor (2). Thus obtained comparative precursor (2) was thermally processed at 180° C. for 30 minutes. Further, particles thereof were fragmented so as to pass through a JIS standard sieve (mesh size is 850 μm), thereby obtaining a comparative water absorbent resin composition (2). Table 4 shows a result obtained by measuring properties of the comparative water absorbent resin composition (2).

Comparative Example 9

A surface treatment agent constituted of a mixture solution obtained by mixing 1.0 g of ethyleneglycol and 3.0 g of pure water was evenly mixed with 100 g of the water absorbent resin (A1) obtained in the Referential Example 6. Thereafter, thus obtained mixture was thermally processed at 180° C. for 30 minutes. Further, particles thereof were fragmented so as to pass through a JIS standard sieve (mesh size is 850 μm), thereby obtaining a comparative water absorbent resin composition (3). Table 4 shows a result obtained by measuring properties of the comparative water absorbent resin composition (3).

In an experiment for clearly showing effects of such surface treatment, it is preferable to compare effects with each other by using the same precursor like the water absorbent resin (A). For example, when the particle size distribution of the precursor varies, it may be impossible to exactly evaluate parameters, such as SFC, which depends on the particle size. Further, in comparing SFCs indicative of performances of the water absorbent resins, it is preferable to compare SFC of a water absorbent resin with SFC of another water absorbent resin having substantially the same CRC as that water absorbent resin.

Table 4 shows that: the water absorbent resin composition (1), obtained in Example 5, whose multivalent metal component (aluminum) concentration in the surface treatment agent is high, has much higher SFC and AAP than those of the comparative water absorbent resin composition (1) obtained in the Comparative Example 7 though the water absorbent resin composition (1) has the same CRC as that of the comparative water absorbent resin composition (1). Further, the water absorbent resin composition (1) obtained in the Example 5 has a lower moisture absorption blocking ratio (B.R) than that of the comparative water absorbent resin composition (1). Thus, the water absorbent resin composition (1) is superior in the moisture absorption blocking property.

According to the present invention, the multivalent metal component concentration in the surface treatment agent is raised, thereby obtaining the water absorbent resin composition having much higher saline flow conductivity (SFC) and moisture absorption blocking property than those of a water absorbent resin composition obtained by a conventional technique, while keeping the same centrifuge retention capacity (CRC) as that of the conventional water absorbent resin composition.

As to the comparative water absorbent resin composition (3) obtained in the Comparative Example 9, it is impossible to obtain the sufficient property by using mere the organic secondary cross-linking agent. That is, the comparative water absorbent resin composition (3) has the same CRC as that of the conventional water absorbent resin composition, but has extremely low SFC and moisture absorption blocking property. Thus, the comparative water absorbent resin composition (3) does not have a sufficient performance.

Example 7

A surface treatment agent constituted of a mixture solution obtained by mixing 0.3 g of 1,4-butanediol, 0.3 g of propyleneglycol, 1 g of pure water, and 0.5 g of aluminum sulfate hydrate (tetradecahydrate to octadecahydrate) (weight average particle diameter was 165 μm, bulk density was 0.86 g/cm$^3$, solubility with respect to pure water of 0° C. was 46.4 wt %) was evenly mixed with 100 g of the water absorbent resin (A2) obtained in the Referential Example 6. Thereafter, thus obtained mixture was thermally processed at 180° C. for 30 minutes. Further, particles thereof were fragmented so as to pass through a JIS standard sieve (mesh size is 710 μm), thereby obtaining a water absorbent resin composition (3). Table 5 shows a result obtained by measuring properties of the water absorbent resin composition (3).

Example 8

A surface treatment agent constituted of a mixture solution obtained by dissolving 0.7 g of ethylenecarbonate and 1.5 g of aluminum sulfate octadecahydrate in 2.2 g of pure water heated to 80° C. was evenly mixed with 100 g of the water absorbent resin (A2) obtained in the Referential Example 6, thereby obtaining a precursor (4). Thus obtained precursor (4) was thermally processed at 180° C. for 30 minutes. Further, particles thereof were fragmented so as to pass through a JIS standard sieve (mesh size is 710 μm), thereby obtaining a water absorbent resin composition (4). Table 5 shows a result obtained by measuring properties of the water absorbent resin composition (4).

Comparative Example 10

A surface treatment agent constituted of a mixture solution obtained by mixing 0.3 g of 1,4-butanediol, 0.3 g of propyleneglycol, 2.73 g of pure water, and 0.5 g of aluminum sulfate hydrate (tetradecahydrate to octadecahydrate) (weight average particle diameter was 165 μm, bulk density was 0.86 g/cm$^3$, solubility with respect to pure water of 0° C. was 46.4 wt %) was evenly mixed with 100 g of the water absorbent resin (A2) obtained in the Referential Example 6, thereby obtaining a comparative precursor (4). Thus obtained comparative precursor (4) was thermally processed at 180° C. for 30 minutes. Further, particles thereof were fragmented so as to pass through a JIS standard sieve (mesh size is 710 μm), thereby obtaining a comparative water absorbent resin composition (4). Table 5 shows a result obtained by measuring properties of the comparative water absorbent resin composition (4).

Comparative Example 11

With reference to Example recited in Published Japanese Translations of International Publication of Patent Application No. 538275/2002 (Tokuhyo 2002-538275) (WO00/53664), the following experiment was performed.

A surface treatment agent constituted of a mixture solution obtained by mixing 0.7 g of ethylenecarbonate, 2.2 g of pure water, and 0.8 g of aluminum sulfate 18 hydrate was evenly mixed with 100 g of the water absorbent resin (A2) obtained in the Referential Example 6. Thereafter, thus obtained mixture was thermally processed at 180° C. for 30 minutes. Further, particles thereof were fragmented so as to pass through a JIS standard sieve (mesh size is 710 μm), thereby obtaining a comparative water absorbent resin composition (5). Table 5 shows a result obtained by measuring properties of the comparative water absorbent resin composition (5).

Comparative Example 12

A surface treatment agent constituted of a mixture solution obtained by mixing 0.3 g of 1,4-butanediol, 0.3 g of propyleneglycol, 0.03 g of ethyleneglycol diglycidyl ether, 1.5 g of pure water, and 1.0 g of aluminum sulfate tetradecahydrate was evenly mixed with 100 g of the water absorbent resin (A4) obtained in the Referential Example 6. Thereafter, thus obtained mixture was thermally processed at 130° C. for 30 minutes. Further, particles thereof were fragmented so as to pass through a JIS standard sieve (mesh size is 710 μm), thereby obtaining a water absorbent resin composition (11). Table 5 shows a result obtained by measuring properties of the water absorbent resin composition (11).

Table 5 shows a result obtained by comparing the Example 8 with the Comparative Example 10 under such condition that ethylene carbonate was used as the organic secondary cross-linking agent and the multivalent metal component concentration in the surface treatment agent was varied. When the solution is at ordinary temperature, it is difficult to prepare the treatment agent having a composition shown in the Example 8 due to the solubility of aluminum sulfate. Thus, in the Example 8, temperature of the treatment agent was raised to 80° C., thereby preparing the treatment agent whose multivalent metal component concentration was high. The water absorbent resin composition (4) obtained in this manner was much superior to the comparative water absorbent resin composition (5) obtained in the Comparative Example 10 in terms of the saline flow conductivity (SFC) and the moisture absorption fluidity.

Example 9

A surface treatment agent constituted of a mixture solution obtained by mixing 0.3 g of 1,4-butanediol, 0.3 g of propyleneglycol, 1.5 g of pure water, and 1.0 g of aluminum sulfate hydrate (tetradecahydrate to octadecahydrate) (weight average particle diameter was 165 μm, bulk density was 0.86 g/cm$^3$, solubility with respect to pure water of 0° C. was 46.4 wt %) was evenly mixed with 100 g of the water absorbent resin (A3) obtained in the Referential Example 6, thereby obtaining a precursor (5). Thus obtained precursor (5) was thermally processed at 180° C. for 30 minutes. Further, particles thereof were fragmented so as to pass through a JIS standard sieve (mesh size is 600 μm), thereby obtaining a water absorbent resin composition (5). Table 6 shows a result obtained by measuring properties of the water absorbent resin composition (5).

Example 10

A surface treatment agent constituted of a mixture solution obtained by mixing 0.3 g of 1,4-butanediol, 0.3 g of propyleneglycol, 1 g of pure water, and 0.5 g of aluminum sulfate hydrate (tetradecahydrate to octadecahydrate) (weight average particle diameter was 165 μm, bulk density was 0.86 g/cm$^3$, solubility with respect to pure water of 0° C. was 46.4 wt %) was evenly mixed with 100 g of the water absorbent resin (A3) obtained in the Referential Example 6. Thereafter, thus obtained mixture was thermally processed at 180° C. for 30 minutes. Further, particles thereof were fragmented so as to pass through a JIS standard sieve (mesh size is 600 μm), thereby obtaining a water absorbent resin composition (6). Table 6 shows a result obtained by measuring properties of the water absorbent resin composition (6).

Example 11

A surface treatment agent constituted of a mixture solution obtained by mixing 1.0 g of ethyleneglycol, 2.0 g of pure water, and 0.8 g of aluminum chloride 6 hydrate was evenly mixed with 100 g of the water absorbent resin (A3) obtained in the Referential Example 6. Thereafter, thus obtained mixture was thermally processed at 210° C. for 20 minutes. Further, particles thereof were fragmented so as to pass through a JIS standard sieve (mesh size is 600 μm), thereby obtaining a water absorbent resin composition (7). Table 6 shows a result obtained by measuring properties of the water absorbent resin composition (7).

Example 12

A surface treatment agent constituted of a solution obtained by dissolving 0.7 g of ethylenecarbonate and 1.2 g of aluminum sulfate 18 hydrate in 2.2 g of pure water heated to 60° C. was evenly mixed with 100 g of the water absorbent resin (A2) obtained in the Referential Example 6. Thereafter, thus obtained mixture was thermally processed at 180° C. for 30 minutes. Further, particles thereof were fragmented so as to pass through a JIS standard sieve (mesh size is 710 μm), thereby obtaining a water absorbent resin composition (8). Table 5 shows a result obtained by measuring properties of the water absorbent resin composition (8).

Example 13

A surface treatment agent constituted of a mixture solution obtained by mixing 0.3 g of 1,4-butanediol, 0.3 g of propyleneglycol, 1 g of pure water, and 0.5 g of aluminum sulfate hydrate (tetradecahydrate to octadecahydrate) (weight average particle diameter was 165 μm, bulk density was 0.86 g/cm³, solubility with respect to pure water of 0° C. was 46.4 wt %) was evenly mixed with 100 g of the water absorbent resin (A3) obtained in the Referential Example 6. Thereafter, thus obtained mixture was thermally processed at 185° C. for 25 minutes. Further, particles thereof were fragmented so as to pass through a JIS standard sieve (mesh size is 600 μm), thereby obtaining a water absorbent resin composition (9). Table 6 shows a result obtained by measuring properties of the water absorbent resin composition (9).

Comparative Example 13

A surface treatment agent constituted of a mixture solution obtained by mixing 0.3 g of 1,4-butanediol, 0.3 g of propyleneglycol, 4.0 g of pure water, and 1.0 g of aluminum sulfate hydrate (tetradecahydrate to octadecahydrate) (weight average particle diameter was 165 μm, bulk density was 0.86 g/cm³, solubility with respect to pure water of 0° C. was 46.4 wt %) was evenly mixed with 100 g of the water absorbent resin (A3) obtained in the Referential Example 6. Thereafter, thus obtained mixture was thermally processed at 180° C. for 30 minutes. Further, particles thereof were fragmented so as to pass through a JIS standard sieve (mesh size is 600 μm), thereby obtaining a comparative water absorbent resin composition (6). Table 6 shows a result obtained by measuring properties of the comparative water absorbent resin composition (6).

Comparative Example 14

A surface treatment agent constituted of a mixture solution obtained by mixing 0.3 g of 1,4-butanediol, 0.25 g of propyleneglycol, 2.73 g of pure water, and 0.5 g of aluminum sulfate hydrate (tetradecahydrate to octadecahydrate) (weight average particle diameter was 165 μm, bulk density was 0.86 g/cm³, solubility with respect to pure water of 0° C. was 46.4 wt %) was evenly mixed with 100 g of the water absorbent resin (A3) obtained in the Referential Example 6, thereby obtaining a comparative precursor (7). Thus obtained comparative precursor (7) was thermally processed at 180° C. for 30 minutes. Further, particles thereof were fragmented so as to pass through a JIS standard sieve (mesh size is 600 μm), thereby obtaining a comparative water absorbent resin composition (7). Table 6 shows a result obtained by measuring properties of the comparative water absorbent resin composition (7).

Comparative Example 15

With reference to Example recited in Published Japanese Translations of International Publication of Patent Application No. 538275/2002 (Tokuhyo 2002-538275) (WO00/53664), the following experiment was performed.

A surface treatment agent constituted of a mixture solution obtained by mixing 0.7 g of ethylenecarbonate, 2.2 g of pure water, and 0.8 g of aluminum sulfate 18 hydrate was evenly mixed with 100 g of the water absorbent resin (A3) obtained in the Referential Example 6. Thereafter, thus obtained mixture was thermally processed at 180° C. for 30 minutes. Further, particles thereof were fragmented so as to pass through a JIS standard sieve (mesh size is 600 μm), thereby obtaining a comparative water absorbent resin composition (8). Table 6 shows a result obtained by measuring properties of the comparative water absorbent resin composition (8).

Comparative Example 16

A surface treatment agent constituted of a mixture solution obtained by mixing 0.32 g of 1,4-butanediol, 0.5 g of propyleneglycol, and 2.73 g of pure water was evenly mixed with 100 g of the water absorbent resin (A3) obtained in the Referential Example 6, thereby obtaining a comparative precursor (9). Thus obtained comparative precursor (9) was thermally processed at 180° C. for 35 minutes. Further, particles thereof were fragmented so as to pass through a JIS standard sieve (mesh size is 600 μm), thereby obtaining a comparative water absorbent resin composition (9). Table 6 shows a result obtained by measuring properties of the comparative water absorbent resin composition (9).

Comparative Example 17

A surface treatment agent constituted of a mixture solution obtained by mixing 0.32 g of 1,4-butanediol, 0.5 g of propyleneglycol, 0.5 g of isopropyl alcohol, and 2.73 g of pure water was evenly mixed with 100 g of the water absorbent resin (A3) obtained in the Referential Example 6, thereby obtaining a comparative precursor (10). Thus obtained comparative precursor (10) was thermally processed at 190° C. for 30 minutes. Further, particles thereof were fragmented so as to pass through a JIS standard sieve (mesh size is 600 μm), thereby obtaining a comparative water absorbent resin composition (10). Table 6 shows a result obtained by measuring properties of the comparative water absorbent resin composition (10).

Table 6 shows that: according to the present invention, the multivalent metal component concentration in the surface treatment agent is raised, thereby obtaining the water absorbent resin composition having much higher saline flow conductivity (SFC) and much higher moisture absorption blocking property than those of a water absorbent resin composition obtained by a conventional technique, while keeping the same centrifuge retention capacity (CRC) as that of the conventional water absorbent resin composition.

Further, Table 7 shows a result obtained by measuring a moisture absorption blocking ratio (wt %) of each comparative precursor, and also shows properties of each corresponding water absorbent resin composition.

Table 7 shows that: as the humidification blocking ratio is smaller, both the SFC and the moisture absorption fluidity of the water absorbent resin composition are higher. On the basis of such characteristic, the inventors of the present invention succeeded in obtaining the water absorbent resin composition, having extremely high saline flow conductivity (SFC) and moisture absorption blocking property while keeping the same centrifuge retention capacity (CRC), by reducing the humidification blocking ratio.

TABLE 3

|  | A1 | A2 | A3 | A4 |
|---|---|---|---|---|
| WATER ABSORBENT RESIN |  |  |  |  |
| D50 (μm) | 480 | 322 | 322 | 315 |
| σζ | 0.388 | 0.380 | 0.359 | 0.47 |
| PARTICLE SIZE DISTRIBUTION |  |  |  |  |
| 850 μm or more (wt %) | 0.0 | 0.0 | 0.0 | 0.0 |
| 850 to 710 μm or more (wt %) | 2.5 | 0.1 | 0.0 | 0.0 |
| 710 to 600 μm or more (wt %) | 25.5 | 0.8 | 0.0 | 0.9 |
| 600 to 500 μm or more (wt %) | 18.3 | 6.9 | 2.7 | 9.0 |
| 500 to 425 μm or more (wt %) | 14.8 | 11.6 | 19.2 | 20.5 |
| 425 to 300 μm or more (wt %) | 21.7 | 39.3 | 36.2 | 23.0 |
| 300 to 212 μm or more (wt %) | 10.9 | 24.4 | 26.6 | 22.9 |
| 212 to 150 μm or more (wt %) | 4.1 | 10.6 | 12.6 | 16.0 |
| 150 to 106 μm or more (wt %) | 1.4 | 4.2 | 2.0 | 4.3 |
| 106 to 45 μm or more (wt %) | 0.6 | 1.7 | 0.6 | 2.1 |
| 45 μm or less (wt %) | 0.2 | 0.4 | 0.1 | 1.3 |
| TOTAL (wt %) | 100.0 | 100.0 | 100.0 | 100.0 |

(A μm or more) represents a water absorbent resin remaining on a sieve whose mesh size is A μm after performing the classification.

(B μm or more) represents a water absorbent passing through a sieve whose mesh size is B μm after performing the classification.

(C to D μm) represents a water absorbent resin which passes through a sieve whose mesh size is C μm and remains on a sieve whose mesh size is D μm after performing the classification.

TABLE 4

| EXAMPLE NUMBER | WATER ABSORBENT RESIN COMPOSITION | REACTION CONDITION | COMPOSITION OF SURFACE TREATMENT AGENT WT % WITH RESPECT TO WATER ABSORBENT RESIN (A) |
|---|---|---|---|
| Referential Example 6 | WATER ABSORBENT RESIN (A) |  |  |
| Example 5 | WATER ABSORBENT RESIN COMPOSITION (1) | 180° C., 30 MINUTES | BD/PG/W/ASH14W = 0.3/0.3/1.5/1.0 |
| Example 6 | WATER ABSORBENT RESIN COMPOSITION (2) | 200° C., 25 MINUTES | EG/W/AlCl$_3$•6W = 1/2/0.8 |
| Comparative Example 7 | COMPARATIVE WATER ABSORBENT RESIN COMPOSITION (1) | 180° C., 30 MINUTES | BD/PG/W/ASH14W = 0.3/0.3/4/1.0 |
| Comparative Example 8 | COMPARATIVE WATER ABSORBENT RESIN COMPOSITION (2) | 180° C., 30 MINUTES | EG/W/ASH14W = 1/3/0.5 |
| Comparative Example 9 | COMPARATIVE WATER ABSORBENT RESIN COMPOSITION (3) | 180° C., 30 MINUTES | EG/W = 1/3 |

| EXAMPLE NUMBER | S/T-[M] Wt % | CRC g/g | SFC ($10^{-7}$·cm$^3$·s$^{-1}$·g$^{-1}$) | AAP g/g | B.R.a wt % | B.R.b wt % | M wt % | Ex wt % |
|---|---|---|---|---|---|---|---|---|
| Referential Example 6 |  | 33.0 |  |  |  |  |  |  |
| Example 5 | 2.93 | 28.2 | 143 | 23.5 | 12 | 16.3 | 8.8 | 6.8 |
| Example 6 | 2.35 | 28.0 | 135 | 24.3 | 21 | 25.3 | 7.4 | 8.2 |
| Comparative Example 7 | 1.62 | 28.4 | 108 | 22.0 | 65 | 62.2 | 5.5 | 7.8 |
| Comparative Example 8 | 1.01 | 28.0 | 98 | 22.5 | 68 | 70.8 | 2.9 | 8.4 |
| Comparative Example 9 |  | 28.1 | 62 | 24.1 | 100 | 98.1 |  | 9 |

TABLE 5

| WATER ABSORBENT RESIN COMPOSITION | REACTION CONDITION | COMPOSITION OF SURFACE TREATMENT AGENT WT % WITH RESPECT TO WATER ABSORBENT RESIN (A) |
|---|---|---|
| WATER ABSORBENT RESIN COMPOSITION (3) | 180° C., 30 MINUTES | BD/PG/W/ASH14–18W = 0.3/0.3/1/0.5 |
| WATER ABSORBENT RESIN COMPOSITION (4) | 180° C., 30 MINUTES | EC/W/ASH18W = 0.7/2.2/1.5 |
| COMPARATIVE WATER ABSORBENT RESIN-COMPOSITION (4) | 200° C., 25 MINUTES | BD/PG/W/ASH14–18W = 0.3/0.3/2.73/0.5 |
| COMPARATIVE WATER ABSORBENT RESIN COMPOSITION (5) | 180° C., 30 MINUTES | EC/W/ASH18W = 0.7/2.2/0.8 |
| COMPARATIVE WATER ABSORBENT RESIN COMPOSITION (11) | 180° C., 30 MINUTES | BD/PG/EGDGE/W/ASH14W = 0.3/0.3/0.03/1.5/1.0 |

| EXAMPLE NUMBER | S/T-[M] wt % | CRC g/g | SFC ($10^{-7} \cdot cm^3 \cdot s \cdot g^{-1}$) | AAP g/g | B.R.a wt % | B.R.b wt % | M wt % | Ex wt % |
|---|---|---|---|---|---|---|---|---|
| Example 7 | 2.04 | 27.0 | 147 | 23.5 | 19 | 23.0 | 6.8 | 7.4 |
| Example 8 | 2.76 | 27.1 | 153 | 22.2 | 17 | 18.0 | 10.3 | 6.5 |
| Comparative Example 10 | 1.12 | 27.2 | 104 | 22.5 | 73 | 78.2 | 3.8 | 8.5 |
| Comparative Example 11 | 2.00 | 27.0 | 118 | 21.3 | 43 | 48.4 | 5.6 | 8.1 |
| Comparative Example 12 | 3.00 | 28.0 | 20 | 18 | 82 | 90 | 5.2 | 9.2 |

TABLE 6

| EXAMPLE NUMBER | WATER ABSORBENT RESIN COMPOSITION | REACTION CONDITION | COMPOSITION OF SURFACE TREATMENT AGENT WT % WITH RESPECT TO WATER ABSORBENT RESIN (A) |
|---|---|---|---|
| Example 9 | WATER ABSORBENT RESIN COMPOSITION (5) | 180° C., 30 MINUTES | BD/PG/W/ASH14–18W = 0.3/0.3/1.5/1.0 |
| Example 10 | WATER ABSORBENT RESIN COMPOSITION (6) | 180° C., 30 MINUTES | BD/PG/W/ASH14–18W = 0.3/0.3/1/0.5 |
| Example 11 | WATER ABSORBENT RESIN COMPOSITION (7) | 210° C., 20 MINUTES | EG/W/AlCl$_3$•6W = 1/2/0.8 |
| Example 12 | WATER ABSORBENT RESIN COMPOSITION (8) | 180° C., 30 MINUTES | EC/W/ASH18W = 0.7/2.2/1.2 |
| Example 13 | WATER ABSORBENT RESIN COMPOSITION (9) | 185° C., 25 MINUTES | BD/PG/W/ASH14–18W = 0.3/0.3/1.5/1.0 |
| Comparative Example 13 | COMPARATIVE WATER ABSORBENT RESIN COMPOSITION (6) | 180° C., 30 MINUTES | BD/PG/W/ASH14–18W = 0.3/0.3/4/1 |
| Comparative Example 14 | COMPARATIVE WATER ABSORBENT RESIN COMPOSITION (7) | 180° C., 30 MINUTES | BD/PG/W/ASH14–18W = 0.32/0.25/2.73/0.5 |
| Comparative Example 15 | COMPARATIVE WATER ABSORBENT RESIN COMPOSITION (8) | 180° C., 30 MINUTES | EC/W/ASH18W = 0.7/2.2/0.8 |
| Comparative Example 16 | COMPARATIVE WATER ABSORBENT RESIN COMPOSITION (9) | 180° C., 35 MINUTES | BD/PG/W = 0.32/0.5/2.73 |
| Comparative Example 17 | COMPARATIVE WATER ABSORBENT RESIN COMPOSITION (10) | 190° C., 30 MINUTES | BD/PG/IPA/W = 0.32/0.5/0.5/2.73 |

| EXAMPLE NUMBER | S/T-[M] wt % | CRC g/g | SFC ($10^{-7} \cdot cm^3 \cdot s \cdot g^{-1}$) | AAP g/g | B.R.a wt % | B.R.b wt % | M wt % | Ex wt % |
|---|---|---|---|---|---|---|---|---|
| Example 9 | 2.76 | 26.0 | 145 | 22.0 | 19 | 21.8 | 8.9 | 6.9 |
| Example 10 | 2.04 | 26.0 | 127 | 22.8 | 24 | 26.9 | 6.6 | 7.7 |
| Example 11 | 2.35 | 26.1 | 138 | 22.3 | 25 | 24.8 | 8.0 | 8.1 |
| Example 12 | 2.37 | 26.0 | 142 | 22.2 | 20.0 | 23.0 | 8.2 | 7.0 |
| Example 13 | 2.76 | 27.5 | 120 | 22 | 25.0 | 26.0 | 9.1 | 7.1 |
| Comparative Example 13 | 1.53 | 26.1 | 105 | 22.9 | 67 | 72.4 | 5.7 | 8.6 |
| Comparative Example 14 | 1.13 | 26.2 | 86 | 23.0 | 83 | 80.9 | 3.9 | 8.5 |
| Comparative Example 15 | 1.75 | 26.3 | 94 | 22.3 | 50 | 53.7 | 5.8 | 7.6 |

TABLE 6-continued

| | | | | | | |
|---|---|---|---|---|---|---|
| Comparative Example 16 | 26.0 | 58 | 23.1 | 100 | 99.9 | 8.8 |
| Comparative Example 17 | 26.2 | 64 | 23.0 | 81 | 85.3 | 9.1 |

TABLE 7

| EXAMPLE NUMBER | PRECURSOR | COMPOSITION OF SURFACE TREATMENT AGENT WT % WITH RESPECT TO WATER ABSORBENT RESIN (A) |
|---|---|---|
| Example 5 | PRECURSOR (1) | BD/PG/W/ASH14W = 0.3/0.3/1.5/1.0 |
| Example 8 | PRECURSOR (4) | EC/W/ASH18W = 0.7/2.2/1.5 |
| Example 10 | PRECURSOR (5) | BD/PG/W/ASH14–18W = 0.3/0.3/1.5/1.0 |
| Comparative Example 8 | COMPARATIVE PRECURSOR (2) | EG/W/ASH14W = 1/3/0.5 |
| Comparative Example 10 | COMPARATIVE PRECURSOR (4) | BD/PG/W/ASH14–18W = 0.3/0.3/2.73/0.5 |
| Comparative Example 14 | COMPARATIVE PRECURSOR (7) | BD/PG/W/ASH14–18W = 0.32/0.25/2.73/0.5 |
| Comparative Example 16 | COMPARATIVE PRECURSOR (9) | BD/PG/W = 0.32/0.5/2.73 |
| Comparative Example 17 | COMPARATIVE PRECURSOR (10) | BD/PG/IPA/W = 0.32/0.5/0.5/2.73 |

| EXAMPLE NUMBER | S/T-[M] wt % | S/T-B.R. wt % | CRC g/g | SFC ($10^{-7} \cdot cm^3 \cdot s \cdot g^{-1}$) | AAP g/g | B.R.a wt % | B.R.b wt % | M wt % | Ex wt % |
|---|---|---|---|---|---|---|---|---|---|
| Example 5 | 2.93 | 32 | 28.2 | 143 | 23.5 | 13 | 16 | 8.8 | 8.6 |
| Example 8 | 2.76 | 34 | 27.1 | 153 | 22.2 | 15 | 18 | 10.3 | 8.5 |
| Example 10 | 2.76 | 40 | 26.0 | 145 | 22.0 | 20 | 22 | 8.9 | 7.8 |
| Comparative Example 8 | 1.01 | 93 | 28.0 | 98 | 22.5 | 63 | 71 | 2.9 | 8.3 |
| Comparative Example 10 | 1.12 | 100 | 27.2 | 104 | 22.5 | 70 | 78 | 3.8 | 9.5 |
| Comparative Example 14 | 1.13 | 100 | 26.2 | 86 | 23.0 | 75 | 81 | 3.9 | 8.7 |
| Comparative Example 16 | | 100 | 26.0 | 58 | 23.1 | 100 | 100 | | 9 |
| Comparative Example 17 | | 86 | 26.2 | 64 | 23.0 | 81 | 85 | | 9.5 |

Signs in Tables 4 to 7 are as follows.
BD: 1,4-butanediol
PG: Propylene glycol
EG: Ethylene glycol
EGDGE: Ethyleneglycol diglycidyl ether
ASH14W: Aluminum sulfate tetradecahydrate
ASH 14-18W: Aluminum sulfate hydrate (tetradecahydrate to octadecahydrate)
ASH18W: Aluminum sulfate octadecahydrate
$AlCl_3$-6W: Aluminum chloride hexahydrate
W: Pure water
S/T-[M]: Concentration (wt %) of a multivalent component included in an aqueous solution of a multivalent metal compound (C)
S/T-B. R: Humidification blocking ratio (wt %)
B. R. a: Moisture absorption blocking ratio a
B. R. b: Moisture absorption blocking ratio b
M: Multivalent metal component extraction rate (wt %)
Ex: Water-soluble component amount (wt %)
V: Absorption rate (second)

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

According to the present invention, it is possible to provide a method for producing such an absorbent that: it is possible to prevent coagulation of the absorbent which causes its fluidity to be lost, and a diffusing property of urine in the absorbent hardly deteriorates in practically using the absorbent of the present invention in an absorber, and performances as the absorber are sufficiently exhibited. Thus, the water absorbent resin of the present invention is favorably used in sanitary materials such as paper diapers, sanitary napkins, incontinence pads, medical pads, and the like.

The invention claimed is:
1. A water absorbent resin composition, comprising:
a particulate water absorbent resin (A) having a cross-linking structure obtained by polymerizing an unsaturated monomer containing an acid group, said particulate water absorbent resin (A) having a cross-linked surface, wherein the water absorbent resin composition contains 95 wt % or more of particles whose particle diameter is less than 850 μm and not less than 106 μm, and a weight average particle diameter of the particles is less than 500 μm and not less than 300 μm, and a logarithmic standard deviation (σζ) of a particle size distribution of the water absorbent resin composition is 0.45 or less, and a water-soluble component of the water absorbent resin composition is 5 wt % or more and 35 wt % or less, the water-soluble component being a value obtained by measuring an amount of the water-soluble component in a water-soluble component extract solution in which the water-soluble component of the water absorbent resin composition is extracted, the water-soluble component extract solution being prepared by adding the water absorbent resin composition to a saline and stirring the mixture thus obtained; and a multivalent metal component, wherein an extraction rate of the multivalent metal component around the surface of said particulate water absorbent resin is 7.6 wt % to 14.8 wt %.

2. The water absorbent resin composition as set forth in claim 1, wherein the particulate water absorbent resin (A) is a particulate water absorbent resin whose surface is cross-linked by a surface cross-linking agent containing a multivalent alcohol.

3. The water absorbent resin composition as set forth in claim 1, wherein a moisture absorption blocking ratio is 30% or less when the water absorbent resin composition is left at 25° C. in a relative humidity of 90% for an hour.

4. The water absorbent resin composition as set forth in claim 1, wherein a centrifuge retention capacity (CRC) at which the water absorbent resin composition absorbs 0.90 wt % of a physiological saline without load for 30 minutes is 25 g/g or more, and a diffusion absorbency (DAP) at which the water absorbent resin composition absorbs 0.90 wt % of a physiological saline at 1.9 kPa for 60 minutes is 20 g/g or more.

5. An absorber, comprising the water absorbent resin composition as set forth in claim 1 and a hydrophilic fiber so that an amount of the water absorbent resin composition (core concentration) is 20 wt % or more with respect to a total amount of the water absorbent resin composition and the hydrophilic fiber.

6. An absorbent article, comprising: the absorber as set forth in claim 5; a liquid-permeable surface sheet; and a liquid-impermeable back sheet.

7. A method for producing a water absorbent resin composition, comprising:

adding a solution of an aqueous multivalent metal compound (B) to a particulate water absorbent resin (A) with a cross-linked surface, said particulate water absorbent resin (A) having a cross-linking structure obtained by polymerizing an unsaturated monomer containing an acid group; and mixing the solution of the aqueous multivalent metal compound (B) with the particulate water absorbent resin (A), wherein the particulate water absorbent resin (A) contains 95 wt % or more of the particles whose particle diameter is less than 850 μm and not less than 106 μm, and a weight average particle diameter of the particles is less than 500 μm and not less than 300 μm, and a logarithmic standard deviation (σζ) of a particle size distribution of the particulate water absorbent resin (A) is 0.45 or less, and a water-soluble component of the particulate water absorbent resin (A) is 35 wt % or less, and an amount of a multivalent metal component contained in the solution of the aqueous multivalent metal compound (B) is 0.001 wt % to 10 wt % with respect to the particulate water absorbent resin (A), and a concentration of the aqueous multivalent metal compound (B) in the solution is 0.40 or more with respect to a saturated concentration of the aqueous multivalent metal compound (B) in the solution, and at least one of a temperature of the particulate water absorbent resin (A) is 50° C. or higher and lower than 100° C., and a temperature of the solution of the aqueous multivalent metal compound (B) is 30° C. or higher and lower than 100° C., and wherein an extraction rate of the multivalent metal component around the surface of said particulate water absorbent resin is 7.6 wt % to 14.8 wt %.

8. A method for producing a water absorbent resin composition, comprising:

mixing a particulate water absorbent resin (A) having a cross-linking structure obtained by polymerizing an unsaturated monomer containing an acid group, a solution of an aqueous multivalent metal compound (B), and an organic surface cross-linking agent (C); and heating a mixture that has been obtained in the mixing step at 150 to 300° C. so as to cross-link a surface of the particulate water absorbent resin (A), wherein the particulate water absorbent resin (A) contains 95 wt % or more of the particles whose particle diameter is less than 850 μm and not less than 106 μm, and a logarithmic standard deviation (σζ) of a particle size distribution of the particulate water absorbent resin (A) is 0.45 or less, and an amount of a multivalent metal component contained in the solution of the aqueous multivalent metal compound (B) is 0.001 wt % to 10 wt % with respect to the particulate water absorbent resin (A), and a concentration of the multivalent metal component contained in a mixed solution including the solution of the aqueous multivalent metal compound (B) and the organic surface cross-linking agent (C) is at least 1.80 wt %, and wherein an extraction rate of the multivalent metal component around the surface of said particulate water absorbent resin is 7.6 wt % to 14.8 wt %.

9. A method for producing a water absorbent resin composition, comprising:

heating a precursor (D) obtained by mixing a particulate water absorbent resin (A) having a cross-linking structure obtained by polymerizing an unsaturated monomer containing an acid group, a solution of a multivalent metal compound (B), and an organic surface cross-linking agent at 150° C. to 300° C. so as to cross-link a surface of the particulate water absorbent resin (A), wherein the particulate water absorbent resin (A) contains 95 wt % or more of the particles whose particle diameter is less than 850 μm and not less than 106 μm, and a logarithmic standard deviation (σζ) of a particle size distribution of the particulate water absorbent resin (A) is 0.45 or less, and an amount of a multivalent metal component contained in the solution of the multivalent metal compound (B) is 0.001 wt % to 10 wt % with respect to the particulate water absorbent resin (A), a concentration of the multivalent metal component contained in a mixed solution including the solution of the multivalent metal compound (B) and the organic surface cross-linking agent is at least 1.80 wt %, and a humidification blocking ratio (wt %) of the precursor (D) is 80 wt % or less, and wherein an extraction rate of the multivalent metal component around the surface of said particulate water absorbent resin is 7.6 wt % to 14.8 wt %.

10. The method as set forth in claim 7, wherein the water absorbent resin composition includes a polymer having a cross-linking structure obtained by polymerizing at least one of acrylic acid and salt thereof.

11. The method as set forth in claim 8, wherein at least one of the solution of the multivalent metal compound (B) and the organic surface cross-linking agent is heated at 30° C. or higher.

12. The method as set forth in claim 8, wherein the organic surface cross-linking agent includes a multivalent alcohol.

13. The method as set forth in claim 8, wherein the multivalent metal component of the multivalent metal compound (B) includes one or more metals selected from bivalent or further multivalent typical metals and transition metals whose group numbers are 4 to 12.

14. The method as set forth in claim 8, wherein the multivalent metal component of the multivalent metal compound (B) is aluminum.

15. The method as set forth in claim 9, wherein at least one of the solution of the multivalent metal compound (B) and the organic surface cross-linking agent is heated at 30° C. or higher.

16. The method as set forth in claim 9, wherein the organic surface cross-linking agent includes a multivalent alcohol.

17. The method as set forth in claim 9, wherein the multivalent metal component of the multivalent metal compound (B) includes one or more metals selected from bivalent or further multivalent typical metals and transition metals whose group numbers are 4 to 12.

18. The method as set forth in claim 9, wherein the multivalent metal component of the multivalent metal compound (B) is aluminum.

19. The method as set forth in claim 8, wherein the water absorbent resin composition includes a polymer having a cross-linking structure obtained by polymerizing at least one of acrylic acid and salt thereof.

20. The method as set forth in claim 9, wherein the water absorbent resin composition includes a polymer having a cross-linking structure obtained by polymerizing at least one of acrylic acid and salt thereof.

21. The water absorbent resin composition as set forth in claim 1, wherein a saline flow conductivity (SFC) is $30 \times 10^{-7} cm^3 s/g$ or more.

22. The water absorbent resin composition as set forth in claim 1, wherein a saline flow conductivity (SFC) is $100 \times 10^{-7} cm^3 s/g$ or more.

23. The water absorbent resin composition as set forth in claim 1, wherein a centrifuge retention capacity (CRC) at which 0.90 wt% of saline is absorbed for 30 minutes without any load is 27 g/g or more and 45 g/g or less.

24. The water absorbent resin composition as set forth in claim 1, wherein an absorbency against pressure (AAP: Absorbency Against Pressure) at which 0.90 wt % of saline is absorbed for an hour under pressure of 0.7 psi (4.83 kPa) is 21 g/g or more and 50 g/g or less.

* * * * *